United States Patent [19]
Bollinger et al.

[11] Patent Number: 5,098,613
[45] Date of Patent: Mar. 24, 1992

[54] ANTI-INFLAMMATORY AGENTS

[75] Inventors: Nancy G. Bollinger; Theodore Goodson, Jr.; David K. Herron, all of Indianapolis, Ind.

[73] Assignee: Eli Lilly and Company, Indianapolis, Ind.

[21] Appl. No.: 551,221

[22] Filed: Jul. 11, 1990

Related U.S. Application Data

[60] Division of Ser. No. 361,373, Jun. 5, 1989, Pat. No. 4,945,099, which is a continuation-in-part of Ser. No. 2,542, Jan. 12, 1987, abandoned.

[51] Int. Cl.$^5$ .................... C11C 1/00; A61K 31/41
[52] U.S. Cl. .................. 260/413; 548/262.2; 544/106; 568/332; 568/333; 568/306; 568/586; 568/637; 568/638; 562/427; 562/471; 562/472; 562/840; 564/171; 564/175
[58] Field of Search ............... 260/413; 568/332, 333, 568/306, 586, 637, 638; 594/106; 562/427, 471, 472, 840; 564/171, 175

[56] References Cited

U.S. PATENT DOCUMENTS

| | | | |
|---|---|---|---|
| 4,166,819 | 9/1979 | Jones et al. | 548/253 |
| 4,507,498 | 3/1985 | Carson et al. | 562/463 |
| 4,661,505 | 4/1987 | Marshall et al. | 514/381 |
| 4,945,099 | 7/1990 | Bollinger et al. | 514/381 |

FOREIGN PATENT DOCUMENTS

| | | |
|---|---|---|
| 1206964 | 7/1986 | Canada . |
| 51819 | 5/1982 | European Pat. Off. . |
| 276065 | 7/1988 | European Pat. Off. . |
| 1493729 | 1/1969 | Fed. Rep. of Germany . |
| 2244324 | 4/1973 | Fed. Rep. of Germany . |
| 3312675 | 10/1983 | Fed. Rep. of Germany . |
| 1111336 | 4/1968 | United Kingdom . |
| 1111337 | 4/1968 | United Kingdom . |
| 1111338 | 4/1968 | United Kingdom . |
| 1387733 | 3/1975 | United Kingdom . |
| 2154586 | 9/1985 | United Kingdom . |

*Primary Examiner*—Jose G. Dees
*Assistant Examiner*—Deborah D. Carr
*Attorney, Agent, or Firm*—Robert A. Conrad; Leroy Whitaker

[57] ABSTRACT

This invention provides benzene derivatives, pharmaceutical formulations of those derivatives, and a method of using the derivatives for the treatment of inflammation in mammals.

14 Claims, No Drawings

ANTI-INFLAMMATORY AGENTS

This application is a division of application Ser. No. 07/361,873, filed June 5, 1989, now U.S. Pat. No. 4,945,099 which is a continuation-in-part of application Ser. No. 07/002,542, filed Jan. 12, 1987, now abandoned.

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently ht to be major components of what has been previously called slow reacting substance of anaphylaxis (SRS-A).

Leukotriene $B_4$ ($LTB_4$) is a proinflammatory lipid which has been implicated in the pathogenesis of psoriasis, arthritis, chronic lung diseases, inflammatory bowe diseases, and other inflammatory states characterized by the infiltration and aggregation of polymorphonuclear leukocytes. Thus aggregated, the polymorphonuclear eukocytes liberate tissue-degrading enzymes and reactive chemicals causing the inflammation. Antagonism of $LTB_4$ should therefore provide a novel therapeutic approach to treatment of these conditions.

It is the object of this invention to provide novel chemical agents which can be used in the treatment of inflammation. Some of the compounds are antagonists of $LTB_4$ and should therefore also be useful in the treatment of conditions such as psoriasis, inflammatory bowel disease, and allergic disorders such as asthma, where leukotrienes are thought to be causal mediators.

SUMMARY OF THE INVENTION

This invention provides Compounds of the Formula I

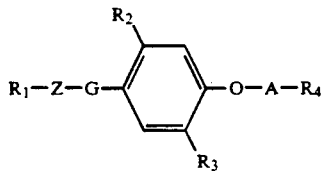

or a pharmaceutically acceptable base addition salt thereof, wherein
$R_1$ is hydrogen or $R'OOC—$;
Z is $—(CH_2)_n—$ or phenylene;
n is 1-8;
G is $—CH_2—$, $—C(=NOH)—$, or

$R_2$ is hydroxy, halo, or $—O—(CH_2)_m—Y$;
$R_3$ is $C_1$-$C_6$ alkyl, $C_1$-$C_6$ alkanoyl, $C_2$-$C_4$ alkenyl, $C_1$-$C_4$ alkoxy, hydroxy-substituted $C_1$-$C_3$ alkyl, or $—CH_2—D$;
A is a bond or straight or branched chain $C_1$-$C_{10}$ alkylidene;
$R_4$ is $C_1$-$C_6$ alkyl, $C_2$-$C_6$ alkenyl, $C_z$-$C_s$ alkynyl, 1,2,4-triazol-1-yl, hydroxy, $—CN$, halo, $—N_3$, $—NR_5R_6$, $—COR_7$, $—S(O)_p—(C_1$-$C_4$ alkyl), 5-tetrazolyl optionally substituted with a $C_1$-$C_4$ alkyl group or $—(CH_2)_q—COOR'$, or phenyl optionally substituted with one or two groups selected from halo, cyano, $C_1$-$C_3$ alkyl, trifluoromethyl, $—CH_2CN$, $—CH_2Br$, $C_1$-$C_4$ alkoxy, $—S(O)_p$-($C_1$-$C_4$ alkyl), acetenyl, $—COOR'$, 5-tetrazolyl, or 5-tetrazolyl substituted with $C_1$-$C_4$ alkyl or $—(CH_2)_q—COOR'$;
where each $R'$ is independently hydrogen or $C_1$-$C_4$ alkyl;
m is 1-4;
q is 1-4;
Y is hydrogen or $—CN$;
D is halo, $C_1$-$C_4$ alkoxy, or $—S—(C_1$-$C_4$ alkyl);
$R_5$ and $R_6$ are independently hydrogen, $C_1$-$C_3$ alkyl, or $C_2$-$C_4$ alkanoyl, or when taken together with the nitrogen atom to which they are attached form a morpholino ring;
$R_7$ is hydroxy, $C_1$-$C_4$ akoxy, halo, $—NR_5R_6$, $—NHOH$ $—N(CH_3)OH$

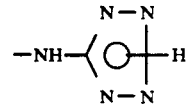

or $C_1$-$C_3$ alkyl; and each p is 0, 1, or 2,
provided that when A is a bond, $R_4$ must be $C_1$-$C_6$ alkyl or an optionally substituted phenyl group, and further provided that when one of $R_5$ and $R_6$ is $C_2$-$C_4$ alkanoyl, the other of $R_5$ and $R_6$ is hydrogen.

Further provided by this invention is a method for treating inflammation comprising the administration of an effective amount of a compound of this invention.

This invention also provides a pharmaceutical formulation which comprises as an active ingredient a compound of this invention as defined above associated with a pharmaceutically acceptable carrier therefor.

DETAILED DESCRIPTION AND PREFERRED EMBODIMENT

The present invention relates to new organic compounds that are useful in the treatment of inflammation. A preferred group of compounds are the compounds of Formula Ia:

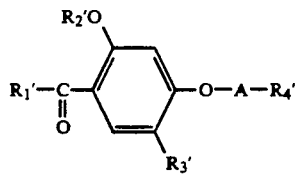

and pharmaceutically acceptable base addition salts thereof wherein
$R_1'$ is methyl or ethyl;
$R_2'$ is hydrogen or methyl;
$R_3'$ is ethyl, propyl, $—CH_2—S—CH_3$, or allyl;
$R_4'$ is hydroxy, cyano, $—COOR'$, $—CONR_5R_6$, $—CO(C_1$-$C_s$ alkyl), $—S(O)_p—(C_1$-$C_4$ alkyl), 5-tetrazolyl optionally substituted with a $C_1$-$C_4$ alkyl group, or phenyl optionally substituted in the meta position with one of the groups listed above, particularly cyano.

The following definitions refer to the various terms used throughout this disclosure.

The term "$C_1$-$C_6$ alkyl" refers to the straight and branched aliphatic radicals of 1 to 6 carbon atoms, such as methyl, ethyl, propyl, isopropyl, butyl, tertbutyl, sec-butyl, isobutyl, pentyl, hexyl, and the like. Within this term are included the terms "$C_1$-$C_3$ alkyl" and "$C_1$-$C_4$ alkyl". The term "$C_1$-$C_4$ alkoxy" refers to methoxy, ethoxy, propoxy, isopropoxy, butoxy, sec-butoxy, isobutoxy, and tert-butoxy. The term "$C_1$-$C_4$ alkoxy" includes within its definition the term "$C_1$-$C_3$ alkoxy". The term "halo" refers to fluoro, chloro, bromo, and iodo.

The term "$C_2$-$C_6$ alkenyl" refers to groups such as vinyl, allyl, butenyl, hexenyl, and the like. The term "$C_2$-$C_6$ alkynyl" refers to groups such as acetenyl, propargyl, butynyl, hexynyl, and the like. The term "$C_1$-$C_6$ alkanoyl" refers to the straight and branched aliphatic acyl radicals of 1 to 6 carbon atoms such as formyl, acety, propionyl, butyryl, 2-methylpropionyl, pentanoyl, hexanoyl, and the like.

The terms "$C_1$-$C_{10}$ alkylidene" and "phenylene" are divalent radicals derived from a $C_1$-$C_{10}$ alkane or benzene, respectively.

When any of the substituents in Formula I are carboxylic acid or 5-tetrazolyl moieties, the compounds of this invention include the pharmaceutically acceptable base addition salts thereof. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

It is recognized that when any of the alkyl groups are branched, various stereoisomeric products may exist. This invention is not limited to any particular stereoisomer but includes all possible individual isomers and mixtures thereof.

The compounds of this invention may be prepared according to standard methods known in the art. For example, final products and intermediates thereto can be prepared by acylating a benzene derivative as summarized in Scheme 1:

Scheme I

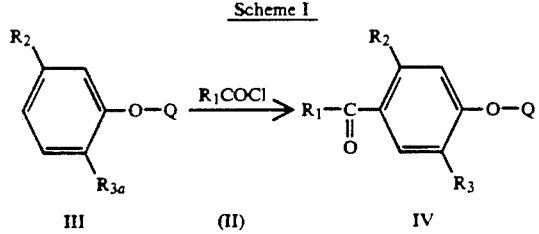

wherein:

$R_{3a}$ is $R_3$ or hydrogen, and Q is —A—$R_4$ or hydrogen. According to this scheme, an acid chloride of formula II is reacted with benzene derivative III under Friedel-Crafts acylation conditions to provide the acyl derivative IV. Any of a number of conditions to effect this transformation are known in the art and are operable. A preferred set of conditions comprises the reaction of II and III with a Lewis acid such as aluminum chloride in the presence of a non-reactive solvent, preferably dichloromethane. The reaction is best carried out at temperatures from about 0 to about 25° C. and is generally complete within 2-4 hours. Alternatively, an acid anhydride or other acid halide may be employed in place of acid chloride III. When $R_{3a}$ is hydrogen, diacylated compounds can be obtained. If two different acyl moieties are desired, such acylations can be performed sequentially.

When Q is hydrogen, the phenol, either before or after acylation, can be alkylated by standard methods. Any other reactive functionality, such as a carboxylic acid or tetrazole, is first protected, for example, by converting the acid to an ester derivative. The phenol is then alkylated with the appropriate alkyl halide X—A—$R_4$, wherein X is a good leaving group such as iodo, bromo, chloro, or mesyl, in the presence of a strong base, such as sodium hydride, and preferably in a non-reactive solvent, such as dimethylformamide. A similar process is used to introduce the —($CH_2$)$_m$—Y functionality at the $R_2$ position when $R_2$ is hydroxy.

Derivatives of Formula IV (or I) which contain an ester or nitrile functionality can be transformed to the corresponding acid and/or tetrazole compounds of the invention according to standard methods. For example, hydrolysis of esters of may be accomplished by any of a variety of acidic or basic conditions, preferably under aqueous conditions. Two preferred methods involve the use of lithium hydroxide in a solvent mixture of acetone/water or potassium hydroxide in a mixture of methanol/water. Under the former conditions, hydrolysis is generally Complete in about 12-18 hours at temperatures from about 20°-30° C. whereas the latter reaction is usually complete in one hour at 20°-30° C.

Similarly, transformation of the nitriles of this invention to the corresponding tetrazoles can be accomplished by any of a variety of standard methods. Generally, the nitrile is reacted with an azide reagent in a non-reactive solvent. Preferred conditions include the use of ammonium azide in dimethylformamide or trinbutylstannylazide in a non-reactive solvent such as dimethoxyethane or tetrahydrofuran. Under the latter conditions, the reaction is generally heated at or near the reflux temperature of the reaction mixture. The transformation is generally complete under these conditions in 2-3 days.

It is generally preferred, in compounds containing both a nitrile and an ester functionality, that the nitrile group be transformed into a tetrazole before hydrolysis of the ester.

When A—$R_4$ or —($CH_2$)$_m$—Y are methyl, the corresponding phenols may be obtained via standard demethylation procedures. Standard methods for this transformation include the use of hydrobromic acid in acetic acid or treatment with molten pyridine hydrochloride. These methods usually also transform a carboxylic acid ester to the corresponding free carboxylic acid.

Other intraconversions of compounds are readily apparent to skilled artisans. For example, when $R_4$ is halo, compounds treated with cyanide, such as potassium or sodium cyanide, in a non-reactive solvent such as dimethylformamide, are transformed into cognates wherein $R_4$ is —CN. The use of a catalytic amount of iodide is employed to speed the reaction. Such nitriles can be converted into tetrazoles as described above, or hydrolyzed in the presence of a base, such as sodium or potassium hydroxides, in alcoholic water to provide the corresponding carboxylic acids. An alternate process for converting halides into nitriles involves the displacement by carbon anions in sodium amide and liquid ammonia as described in Example 68 which follows.

In other intraconversions, the halide derivative of Formula I ($R_4$ is halo) is allowed to react with an azide (e.g., sodium azide), amine (e.q., $R_5R_6NH$), or thiol (e.g., ($C_1$-$C_4$ alkyl)—SH), to provide the analogous compounds wherein $R_4$ is —$N_3$, —$NR_5R_6$, and —S—($C_1$-$C_4$ alkyl), respectively. The appropriate reagent is usually employed in the presence of a non-reactive solvent, such as dimethylformamide, and the transformation is generally complete within about 12-18 hours when kept at approximately 25° C. When a thiol reagent is used, a strong base, such as sodium hydride, is preferably also added. The primary amine compounds (e.g., $R_4$ is —$NH_2$) can also be obtained by reducing the corresponding azide, e.g., through catalytic hydrogenation. The primary amine produced by any of these methods may be acylated by standard means, such as upon treatment with an alkanoyl halide or anhydride in the presence of a non-reactive acid scavenger.

Other transformations are also well known. Carboxylic acids can be esterified by standard means, or converted to acid halides which are then reacted with amines of the formula $R_5R_6NH$, $NH_2OH$, or $NH(CH_3)OH$ to provide the corresponding amides. Similarly, esters, amides, and nitriles may be hydrolyzed to the carboxylic acid by means as described previously. Nitriles can also be hydrolyzed to the primary amide by treatment with aqueous base.

Alkylation of tetrazoles, such as with a $C_1$-$C_4$ alkyl halide X—$(CH_2)_q$—COOR', in the presence of an acid scavenger, such as potassium carbonate, and an inert solvent such as dimethylformamide, provides both 1- and 2-substituted tetrazol-5-yl derivatives which may be separated by standard methods, for example, by employing high pressure liquid chromatography.

Although many of the compounds wherein $R_4$ is hydroxy can be made directly via alkylation of the desired phenol with a halo alkanol, some carbinols may also be obtained by reducing the corresponding ester or ketone, or by alkylating an acid halide derivative as found in Examples 102 and 103 which follow.

Similar transformations may be made with substituents on the optionally substituted phenyl ring of the $R_4$ moiety, and also various substituents accorded to $R_3$. For example, when $R_3$ is alkenyl, the double bond can be oxidized with a peracid to the corresponding epoxide intermediate which, upon catalytic hydrogenation, can be transformed into a hydroxyalkyl derivative. Reduction of an alkanoy derivative also provides a carbinol analog. Hydrogenation of an alkene derivative or further reduction of the carbinol provides the alkyl substituted compound. In the special case of a benzaldehyde being transformed into a methanol, treatment of the methanol with lithium chloride and collidine in dimethylformamide provides the versatile chloromethyl derivative which, upon treatment with an alkanethiol or methanol/silver perchlorate, serves as an intermediate to the alkylthiomethyl and methoxymethyl compounds of this invention, respectively.

The thio derivatives and intermediates of this invention (p is 0) may be transformed into the corresponding sulfoxide (p is 1) compounds upon treatment with a mild oxidizing agent, such as hydrogen peroxide in methanol, meta-chloroperbenzoic acid (MCPBA) in methylene chloride at 0° C., or an alkali metal periodate in aqueous alcohol. The corresponding sulfones (p is 2) are prepared from the thio or sulfoxide compounds on treatment with a strong oxidizing agent such as hydrogen peroxide in acetic acid or m-chloroperbenzoic acid in methylene chloride at 20°-30° C. In addition, various compounds of Formula I can be prepared from other compounds, precursors, or intermediates of Formula I by standard methods such as hydrolysis, esterification, alkylation, oxidation, reduction, and the like, as are well known to those skilled in the art.

Whereas the aforementioned methods for preparing compounds are directed primarily to acyl derivatives (i.e., G=—CO—), these acyl compounds, either final compounds of Formula I or intermediates thereto, can be used for preparing the other compound of this invention. For example, those compounds wherein G is —CO— can be reduced to prepare the corresponding methylene compounds of Formula I (G=—$CH_2$—). A preferred method of accomplishing this transformation involves reduction of the ketone with zinc and acetic acid in the presence of a strong acid such as concentrated hydrochloric acid. This transformation is generally complete in about 10-60 hours when held at ambient temperature. As will be appreciated by one skilled in the art, compounds where $R_4$ is susceptible to reaction with acid may further react under these conditions. Therefore, this reaction is preferably carried out on compounds of Formula I wherein $R_4$ is inert to the reaction conditions. Compounds wherein, for example, $R_4$ is nitrile, halo, azido, or wherein $R_7$ is alkoxy, halo, or various amines, may be transformed into other compounds of this invention (e.g., carboxylic acids) which will then have to be retransformed into the desired final product. Alternatively, the transformation of the ketone to the methylene group may be accomplished through cataytic hydrogenation in the presence of palladium on carbon in solvents such as acetic acid and ethanol.

The ketones of this invention (G=—CO—) can also be transformed into the oximes (G=—C(=NOH)) simply by treatment by hydroxylamine. This reaction is generally carried out in a nonreactive solvent such as methanol. The hydroxylamine is generally added as the hydrochloride salt and then treated with a weak base, such as sodium acetate, to generate the free hydroxylamine in situ. When carried out in the preferred solvent methanol, the reaction is generally complete in about 48 hours when heated at reflux temperature.

Intermediate compounds II and III and any other necessary reagents are either commercially available, known in the literature, or can be prepared according to methods known in the art as exemplified by the examples which follow. The following examples further illustrate the preparation of the intermediates and compounds of this invention. The examples are illustrative only and are not intended to limit the scope of the invention in any way. Where structures were confirmed by infra-red, proton nuclear magnetic resonance, or mass spectral analysis, the compound is so designated by "IR", "NMR", or "MS", respectively.

Preparation 1

2-allyl-4-acetyl-5-methoxyphenol

A. Preparation of 4-allyloxy-2-hydroxyacetophenone.

A mixture of 60.8 g of 2,4-dihydroxyacetophenone, 38.0 ml of allyl bromide, 60.7 g of potassium carbonate, 5 g of potassium iodide, and 500 ml of methyl ethyl ketone was heated at reflux for 24 hours. The mixture was filtered and the filtrate concentrated in vacuo. The residue was dissolved in ethyl acetate/-Skelly B, washed successively with potassium carbonate and sodium chloride solutions, dried over sodium sulfate, filtered; and concentrated in vacuo to provide 69.4 g of the subtitle intermediate as an oil which was used without further purification.

B. Preparation of 4-allyloxy-2-methoxyacetophenone.

To a mixture of 10.6 g of a 50% sodium hydride dispersion in oil and 18.7 ml of methyl iodide in 150 ml of dimethylformamide cooled to 0° C. by means of an external ice bath was added a solution of 38.4 g of 4-allyloxy-2-hydroxyacetophenone in 100 ml of dimethylformamide over a 30 minute interval. The mixture was allowed to warm to room temperature and then heated for 5 hours at 50°-60° C. After cooling, the reaction mixture was added to ethyl acetate and ilute hydrochloric acid. The layers were separated, and the organic layer was washed with a saturated sodium chloride solution, dried over sodium sulfate, filtered, and concentrated in vacuo. The residue was dissolved in a minimum of hot heptane, and on subsequent cooling to room temperature, 13.63 g of the desired subtitle intermediate were recovered, m.p. <25° C.

Analysis for $C_{12}H_{14}O_3$: Calculated: C, 70.23; H, 6.38; Found: C, 70.02; H, 6.56.

C. Preparation of 2-allyl-4-acetyl-5-methoxyphenol.

Under a nitrogen atmosphere, 7.4 of 4-allyl-oxy-2-methoxyacetophenone were heated with stirring at 10° C. After cooling, the residue was dissolved in methylene chloride/heptane and cooled overnight in a freezer (ca −20° C.). The crystals which formed were recovered by filtration affording 1.78 g of the title intermediate. NMR.

Analysis for $C_{12}H_{14}O_3$: Calculated: C, 69.89; H, 6.84; Found: C, 68.81; H, 6.42.

Preparation 2

5-allyl-2,4-dihydroxyacetophenone

To 106 mg of 2-allyl-4-acetyl-5-methoxyphenol in 15 ml of methylene chloride at −78° C. under a nitrogen atmosphere were added 1.5 ml of a 1.0 M solution of boron tribromide in methylene chloride. The mixture was allowed to warm to −45° C. over the next 30 minutes and then added to ethyl acetate and a saturated sodium chloride solution. The layers were separated and the organic layer dried over sodium sulfate, filtered, and concentrated in vacuo. The residue was purified by preparative thin layer chromatography (silica gel) eluting with 40% ethyl acetate in hexane providing 51 mg of the desired title intermediate. Crystallization from diethyl ether/hexane provided material with a melting point of 74°-76° C. NMR.

Preparation 3

6-(5-Ethyl-2,4-dihydroxyphenyl)-6-oxohexanoic acid, methyl ester

To a mixture of 50 ml of a 1M solution of boron tribromide in methyene chloride cooled to 0° C. were added 3.08 g of 6-(5-ethyl-2,4-dimethoxyphenyl)-6-oxohexanoic acid, methy ester (See example 6). While allowing the temperature to warm to room temperature, the mixture was stirred for 24 hours. An additional 25 ml of boron tribromide were added and the mixture was again stirred overnight. The reaction mixture was partitioned between a cold ammonium chloride solution and ethyl acetate. The layers were separated and the organic layer was again washed with cold ammonium chloride solution. The organic layer was dried over sodium sulfate, filtered, and concentrated in vacuo. The residue was dissolved in 200 ml of methanol. Under a nitrogen atmosphere, two milliliters of sulfuric acid were added, and the mixture heated at reflux for three hours. After removing the methanol in vacuo, the residue was dissolved in ethyl acetate, washed twice with a saturated sodium chloride solution, dried over sodium sulfate, filtered, and concentrated in vacuo. The resulting residue was purified by high pressure liquid chromatography over silica gel eluting with a 0-40% ethyl acetate in hexane radiant. The appropriate fractions were combined and concentrated in vacuo to provide 0.36 g of the desired title intermediate, m.p. =62°-64° C.

According to the same procedure (in some cases less the step reforming the ester), the following intermediates were prepared from the corresponding dimethoxy compounds of Examples 1-5, and 7-9.

1-2,4-dihydroxybenzoyl)benzoic acid, methyl ester, 43% yield, m.p. =146°-147° C.

Analysis for $C_{17}H_{16}O_5$: Calculated: C, 67.99; H, 5.37; Found: C, 66.77; H, 5.56.

4-(5-Ethyl-2,4-dihydroxybenzoyl)benzoic acid, methyl ester, 21% yield, m.p. =150°-153° C.

2-(5-Ethyl-2,4-dihydroxybenzoyl)benzoic acid, methyl ester, 39% yield.

5-Butyl-2,4-dihydroxyacetophenone, 64% yield
5-Pentyl-2,4-dihydroxyacetophenone, 53% yield
5-Methyl-2,4-dihydroxyacetophenone, 48% yield
5-(5-Ethyl-2,4-dihydroxyphenyl)-5-oxopentanoic acid, methyl ester, 49% yield
5-Ethyl-2,4-dihydroxyacetophenone, 36% yield
5-Hexyl-2,4-dihydroacetophenone, 70% yield Preparation 4

4,6-Diacetoresorcinol

A mixture of 3 g of 4,6-diacetoresorcinol, dimethyl ether (see Example 10), 50 ml of acetic acid, and 50 ml of 48% hydrobromio acid was refluxed for hours. After concentration in vacuo, the residue was partitioned between ethyl acetate and a saturated sodium chloride solution. The layers were separated and the organic solution was washed with a saturated sodium bicarbonate solution. Evaporation of the solvent provided crude product which was purified by high pressure liquid chromatography over silica gel eluting with a 0-50% ethyl acetate in hexane gradient. The appropriate fractions were combined and concentrated in vacuo to provide 0.9 g of the desired title intermediate, m.p. =182°-184° C.

Analysis for $C_{10}H_{10}O_4$: Calculated: C, 61.85; H, 5.19; Found: C, 62.74; H, 5.45.

Preparation 5

5-Acetyl-2,4-dihydroxybenzaldehyde

To a mixture of 49.8 g of 2,4-dimethoxybenzaldehyde, 23.6 ml of acetyl chloride, and 1000 ml of methylene chloride cooled to approximately 0° C. were added 119.7 g of aluminum chloride with stirring under a nitrogen atmosphere. The reaction was allowed to warm to room temperature while stirring overnight. The mixture was added to a slurry of ice and concentrated hydrochloric acid. The organic layer was separated and washed with a saturated sodium chloride solution, dried over sodium sulfate, and concentrated in vacuo. The residue was purified by high pressure liquid chromatography over silica gel eluting with a 0–40% ethyl acetate in hexane gradient. The appropriate fractions were pooled and concentrated to provide 5.85 g of the desired title intermediate, m.p. = 142°–143° C.

Preparation 6

5-Acetyl-2,4-dihydroxybenzyl alcohol

One gram of 5-acetyl-2,4-dihydroxybenzaldehyde was hydrogenated in the presence of 1 g of 10% palladium on carbon in 150 ml of ethanol. After about 1 hour, hydrogen uptake ceased and hydrogenation was terminated. The reaction mixture was filtered and concentrated in vacuo. The residue was dissolved in approximately 30 ml of ethyl acetate and cooled in the refrigerator. The resulting solid was recovered by filtration affording 0.66 g of the desired title intermediate, m.p. = 151°–152° C. The same reaction when run on a 5-fold scale provide 2.76 g of material.

Analysis for $C_9H_{10}O_4$: Calculated: C, 59.34; H, 5.53; Found: C, 59.29; H, 5.74.

EXAMPLE 1

5-Butyl-2,4-dimethoxyacetophenone

A. Preparation of 2,4-dimethoxybutyrophenone

One hundred grams of meta-dimethoxybenzene and 84.86 g of butyryl chloride were added to 1000 ml of methylene chloride. The solution was cooled to 0° C. by means of an external acetone/ice bath. With stirring, 144.76 g of aluminum chloride were added in portions over 1 hour. After all of the aluminum chloride was added, the mixture was stirred at 0° C. for 2.5 hours. The mixture was poured into a mixture of ice and concentrated hydrochloric acid. The layers were separated and the organic layer was washed sequentially with a saturated potassium carbonate solution and a saturated sodium chloride solution, dried over magnesium sulfate, and concentrated in vacuo providing 142.3 g of a crude oil which was used in the subsequent reaction without further purification.

B. Preparation of 1-(2,4-dimethoxyphenyl)-1-butanol.

The 142.3 % of crude product from Example 1A were dissolved in 800 ml of methanol. After cooling to approximately 0° C., 31.02 g of sodium borohydride were added in portions. The reaction mixture was allowed to warm to room temperature and stirred overnight. An additional 6.46 g of sodium borohydride were added and the reaction was stirred for 2 days at room temperature. The reaction mixture was heated at reflux for three hours and then concentrated in vacuo. The residue was triturated with cold 1N hydrochloric acid and extracted into ethyl acetate. The organic layer was washed with water, dried over magnesium sulfate, and concentrated in vacuo to provide 137.5 g of the subtitle intermediate which was used without further purification.

C. Preparation of 1-butyl-2,4-dimethoxybenzene.

In five portions, 137.5 g of the intermediate of Example 1B were catalytically hydrogenated in glacial acetic acid. Each portion employed about 5 g of 5% palladium on carbon as the catalyst. Hydrogenation 25 of each portion was complete within about 30–40 minutes. The reactions were combined, filtered, and concentrated in vacuo. The residue was triturated with cold 1N hydrochloric acid and treated with ethyl acetate. The layers were separated and the organic layer was washed with a sodium bicarbonate solution followed by a sodium chloride solution. After drying over magnesium sulfate, the solution was concentrated in vacuo to provide 106.1 g of the desired subtitle intermediate which was used in the subsequent step without further purification.

D. Preparation of 5-butyl-2,4-dimethoxyacetophenone

The 106.1 g of intermediate from Example 1C and 42.87 g of acetyl chloride were dissolved in 1000 ml of methylene chloride. The reaction mixture was cooled to −15° C. by means of an external ethylene glycol/dry ice bath. In portions, 80.06 g of aluminum chloride were added over 90 minutes at a rate to maintain the temperature between −12° and −18° C. The reaction mixture was poured into a mixture of ice and concentrated hydrochloric acid. The layers were separated and the organic layer was washed with a potassium carbonate solution followed by a saturated sodium chloride solution. After drying over magnesium sulfate, the organic solution was concentrated in vacuo to provide 120.1 g of an oil which solidifed upon standing. Twenty grams of this material was purified by high pressure liquid chromatography over silica gel eluting with a 0–100% ethyl acetate and hexane step gradient to provide 8.42 g of the purified title product.

EXAMPLES 2–9

Following the procedure of Example 1D, the following compounds were prepared from the appropriate benzene derivative and the corresponding acid chloride or acid anhydride.

2. 5-Hexyl-2,4-dimethoxyacetophenone, 39% yield.
3. 5-Pentyl-2,4-dimethoxyacetophenone, 19% yield.
4. 5-Methyl-2,4-dimethoxyacetophenone, 32% yield. 5. 3-(5-Ethyl-2,4-dimethoxybenzoyl)benzoic acid, methyl ester, 63% yield, m.p. = 116°–118° C.

Analysis for $C_{19}H_{20}O_5$: Calculated: C, 69.50; H, 6.14; Found: C, 67.59; H; 5,43.

6. 6-(5-Ethyl-2,4-dimethoxyphenyl)-6-oxohexanoic acid, methyl ester, 56% yield, m.p. = 57°–58° C.

Analysis for $C_{17}H_{24}O_5$: Calculated: C, 66.21; H, 7.85; Found: C, 63.09; H, 6.57.

7. 4-(5-Ethyl-2,4-dimethoxybenzoyl)benzoic acid, methyl ester, 53% yield, m.p. = 128°–130° C.

Analysis for $C_{19}H_{20}O_5$: Calculated: C, 69.50; H, 6.14; Found: C, 67.62; H, 7.38.

8. 2-(5-Ethyl-2-hydroxy-4-methoxybenzoyl)-benzoic acid. 24% yield, m.p. = 194°–197° C.

Analysis for $C_{17}H_{16}O_5$; Calculated: C, 67.99; H, 5.37; Found: C, 67.70; H, 5.65.

9. 5-(5-Ethyl-2-hydroxy-4-methoxyphenyl)-5-oxopentanoic acid, 29% yield, m.p. = 124°–128° C.

Analysis for $C_{14}H_{18}O_5$: Calculated: C, 63.14; H, 6.81; Found: C, 64.48; H, 7.22.

EXAMPLE 10

4,6-Diacetoresorcinol, dimethyl ether

Following the general procedure of Example 1D, 100 g of meta-dimethoxybenzene, 62.5 g of acetyl chloride, and 106.16 g of aluminum chloride were reacted in 1000 ml of dichloromethane. After workup, the material was crystallized from ethyl acetate/hexane to provide 89.8 g of crude material. Forty-five grams of this material was purified by high pressure liquid chromatography over silica gel eluting with a 0–20% ethyl acetate i hexane gradient. The less polar material was recovered and identified as 2,4-dimethoxyacetophenone. The material remaining on the chromatography column was eluted with ethyl acetate and provided 10 g of the desired title product.

EXAMPLES 11–15

The following compounds were prepared from the appropriate benzene derivative and corresponding acid chloride or acid anhydride according to the procedure of Example 1D.

11. 5-Acetyl-2,4-dihydroxybenzaldehyde, 12.8% yield, m.p. =134°–136° C.

Analysis for $C_9H_8O_4$: Calculated: C, 60.00; H, 4.98; O, 35.52; Found: C, 59.87; H, 4.55; O, 35.61.

12. 5-[4-(4-Cyanobutoxy)-5-allyl-2-methoxyphenyl]-5-oxopentanoic acid, 8.4% yield.

13. 5-(2-Allyl-4-propanoyl-5-methoxyphenoxy)-pentanenitrile, 22.8% yield.

Analysis for $C_{18}H_{23}NO_3$: Calculated: C, 71.73; H, 7.69; N, 4.65; Found: C, 71.56; H, 7.59; N, 4.44.

14. 5-(2-Allyl-4-benzoyl-5-methoxyphenoxy)-pentanenitrile, 11.2% yield.

15. 5-(4-Acetyl-5-chloro-2-propylphenoxy)-pentanenitrile, 40.8% yield, oil.

Analysis for $C_{16}H_{20}ClNO_2$; Calculated: C, 65.41; H, 6.86; N, 4.77; Cl, 12.07; Found: C, 66.26; H, 7.06; N, 5.04; Cl, 11.84.

EXAMPLE 16

5-(2,4-Diacetyl-5-hydroxy-phenoxy)pentanenitrile

A mixture of 582 mg of 4,6-diacetylresorcinol, of potassium carbonate, 530 mg of 5-bromopentanenitrile and 0.2 g of potassium iodide was heated at reflux overnight. The mixture was concentrated in vacuo and partitioned between ethyl acetate and dilute hydrochloric acid. The organic layer was separated, dried over sodium sulfate, and concentrated in vacuo. The residue was purified by preparative thin layer raphy on silica gel eluting with 40% ethyl etate in hexane to provide 200 mg of the desired title product, m.p. =105°–106° C.

Analysis for $C_{15}H_{17}NO_4$: Calculated: C, 65.44; H, 6.22; N, 5.09; Found: C, 65.61; H, 6.28; N, 5.33.

EXAMPLES 17–67

The following compounds were prepared according to the procedure of Example 16 employing the appropriate pheno and the corresponding halo alkane derivative.

17. 5- 4-Acetyl-5-hydroxy-2-(hydroxymethyl)-phenoxy]pentanenitrile, 44% yield, m.p. =72°–74° C. Analysis for $C_{14}H_{17}NO_4$: Calculated: C, 63.87; H, 6.51; N, 5.32; Found: C, 63.67; H, 6.34; N, 5.31.

18. 5-(4-Acetyl-5-hydroxy-2-formylphenoxy)-pentanenitrile, 3% yield.

Analysis for $C_{14}H_{15}NO_4$: Calculated: C, 64.36; H, 5.79; Found: C, 63.04; H, 6.02.

19. 5-(4-Acetyl-2-ethyl-5-hydroxyphenoxy)-pentanenitrile, 50% yield, m.p. =83°–84.5° C. Analysis for $C_{15}H_{19}NO_3$: Calculated: C, 68.94; H, 7.33; N, 5.36; Found: C, 69.74; H, 6.94; N, 5.17.

20. 7-(4-Acetyl-2-ethyl-5-hydroxyphenoxy)-heptanenitrile, 50% yield, m.p. =56°–57° C.

Analysis for $C_{17}H_{23}NO_3$: Calculated: C, 70.56; H, 8.01; N, 4.84; Found: C, 70.60; H, 8.31; N, 4.70.

21. 6-(4-Acetyl-5-hydroxy-2-allylphenoxy)-hexanenitrile, 45.8% yield, m.p. =70°–71° C.

Analysis for $C_{17}H_{21}NO_3$: Calculated: C, 71.06; H, 7.37; N, 4.87; Found: C, 70.87; H, 7.47; N, 4.70.

22. 5,5'-[(4-Acetyl-6-formyl-1,3-phenylene)-bis(oxy)]-bis[pentanenitrile], 75% yield, m.p. =86°–88° C.

Analysis for $C_{19}H_{22}N_2O_4$: Calculated: C, 66.65; H, 6.48; N, 8.18; Found: C, 66.98; H, 6.25; N, 7.96.

23. 9-(4-Aoetyl-5-hydroxy-2-allylphenoxy)-nonanenitrile, 6% yield, m.p. =50°–52° C.

Analysis for $C_{20}H_{27}NO_3$: Calculated: C, 72.92; H, 8.26; N, 4.25; Found: C, 72.65; H 8.49; N, 4.00. 24. 7-(4-Acetyl-5-hydroxy-2-allylphenoxy)-Analysis for $C_{18}H_{23}NO_3$: Calculated: C, 71.73; H, 7.69; N, 4.65; Found C, 71.85; H, 7.66; N, 4.51.

25. (4-Acetyl-5-hydroxy-2-allylphenoxy)-acetonitrile, 45% yield, m.p. =66°–68° C.

Analysis for $C_{13}H_{13}NO_3$: Calculated: C, 67.52; H, 5.67; N, 6.06; Found: C, 67.31; H, 5.39; N, 5.92.

26. 4-(4-Acetyl-5-hydroxy-2-allylphenoxy)-butanenitrile, 7% yield, m.p. =92°–94° C.

Analysis for $C_{15}H_{17}NO_3$: Calculated: C, 69.48; H, 6.61; N, 5.40; Found: C, 69.96; H, 7.74; N, 6.46.

27. 5-[4-(4-Cyanobutoxy)-5-ethyl-2-hydroxybenzene]-5-oxopentanoic acid, methyl ester, 79% yield m.p.=50°–52° C.

Analysis for $C_{19}H_{25}NO_5$: Calculated: C, 65.69; H, 7.25; N, 4.03; Found: C, 65.82; H, 7.48; N, 4.26. 28. 5-(4-Acetyl-2-methyl-5-hydroxyphenoxy)-pentanenitrile, 71% yield, m.p. =86°–87° C.

Analysis for $C_{14}H_{17}NO_3$: Calculated: C, 68.00; H, 6.93; N, 5.66: Found: C, 67.77; H, 6.84;

29. 5-(4-Acetyl-2-hexyl-5-hydroxyphenoxy)-pentanenitrile, 75% yield, m.p. =45°–49° C.

Analysis for $C_{19}H_{27}NO_3$: Calculated: C, 71.89; H, 8.57; N, 4.41; Found: C, 71.82; H, 8.74; N, 4.29.

30. 5-(4-Acetyl-2-butyl-5-hydroxyphenoxy)-pentanenitrile, 73% yield, m.p. 57°–60° C.

Analysis for $C_{17}H_{23}NO_3$: Calculated: C, 70.56; H, 8.01; N, 4.84; Found: C, 70.79; H, 7.79; N, 4.89.

31. 5-(4-Acetyl-5-hydroxy-2-pentylphenoxy)-pentanenitrile, 58% yield, m.p. =34°–37° C.

Analysis for $C_{18}H_{25}NO_3$: Calculated: C, 71.26; H, 8.31; N, 4.62; Found: C, 71.49; H, 8.41; N, 4.70.

32. 6-[4-(4-Cyanobutoxy)-5-ethyl-2-hydroxy-benzene]-6-oxohexanoic acid, methyl ester, 77.8% yield, m.p. =90°–94° C.

33. 2-[4-(4-Cyanobutoxy)-5-ethyl-2-hydroxy-benzoyl]benzoic acid, methyl ester, 31.5% yield.

34. 3-[4-(4-Cyanobutoxy)-5-ethyl-2-hydroxy-benzoyl]benzoic acid, methyl ester, 85.7% yield, m.p. =88°–90° C.

35. 4-[4-(4-Cyanobutoxy)-5-ethyl-2-hydroxy-benzoyl]benzoic acid, methyl ester, 31.5% yield.

36. 7-[4-Acetyl-5-hydroxy-2-(hydroxymethyl)-phenoxy]heptanenitrile, 69% yield, m.p. =58°–60° C.

Analysis for $C_{16}H_{21}NO_4$: Calculated: C, 65.96; H, 7.27; N, 4.81; Found: C, 65.96; H, 7.04; N, 4.70

37. 4-(Heptyloxy)-2-hydroxy-5-allylacetophenone, 40% yield, oil.

Analysis for $C_{18}H_{26}O_3$: Calculated: C, 74.45; H, 9.02: Found: C, 74.31; H, 8.79.

38. 4-(Octyloxy)-5-allyl-2-hydroxyacetophenone, 21% yield, oil.

Analysis for $C_{19}H_{28}O_3$: Calculated: C, 74.96; H, 9.27; Found: C, 74.99; H, 9.00.

39. 4-(Hexyloxy)-2-hydroxy-5-allylacetophenone, yield, m.p. =42°–44° C.

Analysis for $C_{17}H_{24}O_6$: Calculated: C, 73.88; H, 8.75; Found: C, 73.96; H, 8.93.

40. 4-Butoxy-2-hydroxy-5-allylacetophenone, 60% yield, oil.

Analysis for $C_{15}H_{20}O_3$: Calculated: C, 72.55; H, 8.12; Found: C, 72.60; H, 7.83.

41. 4-Pentyloxy-2-hydroxy-5-allylaceto-phenone, 44% yield, oil.

Analysis for $C_{16}H_{22}O_3$: Calculated: C, 73.25; H, 8.45; Found: C, 73.52; H, 8.41.

42. 2-Hydroxy-4-methoxy-5-allylacetophenone, yield.

Analysis for $C_{12}H_{14}O_6$: Calculated: C, 69.89; H, 6.84; Found: C, 69.87; H, 6.72.

43. 2,4-Dimethoxy-5-allylacetophenone, 2%

Analysis for $C_{13}H_{16}O_3$: Calculated: C, 70.89; H, 7.32; Found: C, 70.14: H, 7.00.

44. 4-(4-Hydroxybutoxy)-5-allyl-2-huydroxyaoetophenone, 5% yield, m.p. =117°-119° C.

Analysis for $C_{15}H_{20}O_4$: Calculated: C, 68.16; H, 7.63; Found: C, 68.38; H, 7.85.

45. 4-(3-Butenyloxy)-2-hydroxy-5-allylacetophenone, 26% yield, m.p. =<25° C.

Analysis for $C_{15}H_{18}O_3$: Calculated: C, 73.15; H, 7.37; Found: C, 72.88; H, 7.45.

46. 4-(5-Hexenyloxy)-2-hydroxy-5-allylacetophenone, 30% yield, m.p. =<25° C.

Analysis for $C_{17}H_{22}O_3$: Calculated: C, 74.42; H, 8.08; Found: C, 74.16; H, 8.13.

47. 2-Hydroxy-4-benzyloxy-5-allylacetophenone, 60% yield, m.p. =86° C.

Analysis for $C_{18}H_{18}O_3$: Calculated: C, 76.57; H, 6.43; Found: C, 76.47; H, 6.19.

48. 4[(4-Acetyl-5-hydroxy-2-allylphenoxy)-methyl]-benzonitrile, 63% yield, m.p. =158.5°-159° C.

Analysis for $C_{19}H_{17}NO_3$: Calculated: C, 74.25; H, 5.58; N, 4.56; Found: C, 74.48; H, 5.80; N, 4.67.

49. 2-[(4-Acetyl-5-hydroxy-2-allylphenoxy)-methyl]-benzonitrile, 71% yield, m.p. =159° C.

Analysis for $C_{19}H_{17}NO_3$: Calculated: C, 74.25; H, 5.58; N, 4.56; Found: C, 74.37; H, 5.86; N, 4.39.

50. 3-[( -Acetyl-5-hydroxy-2-allylphenoxy)-methyl]-benzonitrile, 51% yield, m.p. =131.5° C.

Analysis for $C_{19}H_{17}NO_3$: Calculated C, 74.25; H, 5.58; N, 4.56; Found: C, 74.39; H, 5.55; N, 4.28.

51. 2-Hydroxy-4-(3-methylbenzyloxy)-5-allyl-acetophenone, 50% yield, m.p. =87°-88° C.

Analysis for $C_{19}H_{20}O_3$: Calculated: C, 77.00; H, 6.80; Found: C, 77.03; H, 7.05.

52. -[4-(Bromomethyl)benzyloxy]-2-hydroxy-5-allylacetophenone, 18% yield, oil.

Analysis for $C_{19}H_{19}BrO_3$: Calculated: C, 60.81; H, 5.10; Br, 21.29; Found: C, 60.74; H, 5.11; Br, 21.57.

53. 2-Hydroxy-4-(3-phenylpropoxy)-5-propyl-acetophenone, 26% yield, m.p. =60° C.

Analysis for $C_{20}H_{24}O_3$: Calculated: C, 76.89; H, 7.74; Found: C, 76.68; H, 7.69.

54. 5-Ethyl-4-(3-fluorobenzyloxy)-2-hydroxy-acetophenone, 18% yield, m.p. =104°-105° C.

Analysis for $C_{17}H_{17}OF_3$: Calculated: C, 70.82; H, 5.94; Found: C, 70.54; H, 6.10.

55. 3- -Acetyl-2-ethyl-5-hydroxyphenoxy)-methyl]-benzonitrile, 80% yield, m.p. =155-°155.5° C.

Analysis for $C_{18}H_{17}NO_3$: Calculated: C, 73.20; H, 5.80; N, 4.74; Found: C, 72.92; H, 5.98; N 4.68.

56. 4-(3-Chlorobenzyloxy)-5-ethyl-2-hydroxyacetophenone, 47% yield.

Analysis for $C_{17}H_{17}ClO_3$: Calculated: C, 67.00; H, 5.62; Found: C, 67.13; H, 5.33.

57. 4-(5-Hexynyloxy)-2-hydroxy-5-allylaceto-phenone, 20% yield, m.p. =<25° C. NMR.

58. 5-Ethyl-2-hydroxy-4-(3-trifluoromethyl-benzyloxy)acetophenone, 11% yield.

Analysis for $C_{18}H_{17}F_3O_3$: Calculated: C, 63.90; H, 5.06; Found: C, 62.9; H, 5.53.

59. 4-(3-Methylmercaptobenzyloxy)-5-ethyl-2-hydroxyacetophenone, 18.5% yield, m.p. =89° C. NMR.

60. 3-[(4-Acetyl-5-hydroxy-2-allylphenoxy)-methyl]-benzeneacetonitrile. NMR.

61. -(2-Bromoethoxy)-5-ethyl-2-hydroxy-acetophenone, 42.5% yield, m.p. =58°-59° C. NMR.

62. -(3-Bromopropoxy)-5-ethyl-2-hydroxyacetophenone, 80.3% yield, m.p. =126°-127° C. NMR.

63. 4-(5-Bromopentoxy)-5-ethyl-2-hydroxyacetophenone, 59.7% yield, m.p. =60°-62° C. NMR.

64. 4-(10-Bromodecyloxy)-5-allyl-2-hydroxyacetophenone, 18% yield, m.p. =<25° C. NMR.

Analysis for $C_{21}H_{31}BrO_3$: Calculated: C, 61.31; H, 7.60; Br, 19.42; Found: C, 58.76; H, 6.59; Br, 21.02.

65. 4-(7-Bromoheptyloxy)-5-allyl-2-hydroxyacetophenone, 70% yield, oil.

Analysis for $C_{18}H_{25}BrO_3$: Calculated: C, 58.54; H, 6.82; Br, 21.64; Found: C, 56.92; H, 6.33; Br, 22.32.

66. 4-(6-Bromohexyloxy)-5-allyl-2-hydroxyacetophenone, 42% yield.

Analysis for $C_{17}H_{23}BrO_3$: Calculated: C, 57.47; H, 6.53; Br, 22.49; Found: C, 57.37; H, 6.63; Br, 22.60.

67. 4-(4-Bromobutoxy)-5-allyl-2-hydroxyacetophenone, 56% yield, m.p. =<25° C.

Analysis for $C_{15}H_{19}BrO_3$: Calculated: C, 55.03; H, 5.85; Br, 24.42; Found: C, 54.43; H, 5.87; Br, 24.93.

EXAMPLE 68

4-(6-Cyano-6-methylheptyloxy)-5-ethyl-2-hydroxyacetophenone

Approximately 300 ml of ammonia were condensed in a liter flask fitted with a mechanical stirrer and reflux condenser. A pinch of ferric chloride was added to the solution with stirring followed by the piece-wise addition of 0.69 g of sodium metal. A solution of 1.36 ml of isobutyronitrile in 30 ml of diethyl ether was added dropwise followed by a slurry of 4.935 g of 4-(5-bromopentoxy)-5-ethyl-2-hydroxyacetophenone in diethyl ether. The reaction was stirred overnight during which time the ammonia evaporated leaving an oil. The oil was partitioned between ethyl acetate and dilute cold hydrochloric acid. The organic layer was separated, dried over sodium sulfate, filtered, and concentrated in vacuo. The residue was purified by high pressure liquid chromatography over silica gel eluting with a 0-25% ethyl acetate in hexane gradient providing 2.91 g of the desired title product, m.p. =168°-169° C.

Analysis for $C_{19}H_{27}NO_3$: Calculated: C, 71.89; H, 8.57; N, 4.41; Found: C, 71.58; H, 8.70; N, 4.08.

EXAMPLE 69

8-(4-Acetyl-5-hydroxy-2-allylphenoxy)octanenitrile

A mixture of 1.845 g of 4-(7-bromoheptyloxy5-allyl-2-hydroxyacetophenone, 0.651 g of potassium cyanide, 0.2 g of potassium iodide, and 25 ml of dimethylformamide was heated at 70° C. for approximately 6 days. The mixture was then partitioned between ethyl acetate and cold dilute hydrochloric acid. The layers were separated and the organic layer was dried over sodium sulfate, filtered, and concentrated in vacuo. The residue was purified by preparative thin layer chromatography on silica gel. Purification of the resulting material by crystallization from diethyl ether/hexane provided 190 ml of the desired title product, m.p. =46°–48° C.

Analysis for $C_{19}H_{25}NO_3$: Calculated: C, 72.35; H, 7.99; N, 4.44; Found: C, 72.29; H, 7.72; N, 4.64.

EXAMPLES 70 AND 71

The following compounds are prepared according to the procedure of Example 69 from the appropriate bromide derivative and potassium or sodium cyanide.

70. 11-(4-Acetal-5-hydroxy-2-allylphenoxy)-undecanenitrile, 3.9% yield.

Analysis for $C_{22}H_{31}NO_3$: Calculated: C, 73.92; H, 8.74; N, 3.92; Found: C, 73.83; H, 8.53; N, 3.93.

71. 4-[(4-Acetyl-5-hydroxy-2-allylphenoxy)-methyl]-benzeneacetonitrile, 20% yield, m.p. =142°–144° C. NMR.

EXAMPLE 72

4-(3-Azidopropoxy)-5-ethyl-2-hydroxyacetophenone

A mixture of 2.107 g of 4-(3-bromopropoxy)--ethyl-2-hydroxyacetophenone and 0.5 9 of sodium azide in 30 ml of dimethylformamide was stirred together overnight at room temperature. The mixture was partitioned between ethyl acetate and dilute hydrochloric acid. The layers were separated and the organic layer was dried over sodium sulfate, filtered, and concentrated in vacuo providing the desired title product. The proton NMR and mass spectral analyses were consistent with the structure of the desired product.

EXAMPLE 73

4-(2-Azidoethoxy)-5-ethyl-2-hydroxyacetophenone

The title product was prepared from 2 g of 4-(2-bromoethoxy)-5-ethyl-2-hydroxyacetophenone according to the procedure of Example 72. The proton nmr and mass spectral analyses were consistent with the structure of the desired product.

EXAMPLE 74

4-(4-Aminobutoxy)-2-hydroxy-5-propylacetophenone hydrochloride

A mixture of 1.64 g of 4-(4-bromobutoxy)-2-hydroxy-5-allylacetophenone and 0.325 g of sodium azide and 25 ml of imethylformamide was reacted according to the procedure of Example 72. After workup, the resulting product was hydrogenated over 1 g of 5% palladium on carbon in 100 ml of 2B ethanol for 4 hours. The reaction mixture was filtered and concentrated in vacuo. The residue was dissolved in diethyl ether and extracted into acid. The acidic portion was made basic and extracted into diethyl ether. The organic solution was dried over sodium sulfate and concentrated in vacuo. The residue was dissolved in diethyl ether and hydrogen chloride gas was bubbled through the solution. Evaporation of the solvent and crystallization of the residue from ethanol/diethyl ether provided 0.36 g of the desired product, m.p. =87°–88° C.

Analysis for $C_{15}H_{23}NO_3.HCl$: Calculated: C, 60.10; H, 7.40; N, 4.67; Found: C, 60.22; H, 7.60; N, 4.68.

EXAMPLE 75

2-Hydroxy-4-[4-(4-morpholino)butoxy]-5-allylacetophenone hydrochloride

A mixture of 1.64 g of 4-(4-bromobutoxy)-5-allyl-2-hydroxyacetophenone and 15 ml of morpholine were stirred overnight. Diethyl ether was added and the solution was washed twice with a saturated sodium chloride solution. The organic layer was extracted with cold dilute hydrochloric acid. The acid solution was made basic with potassium carbonate and extracted with diethyl ether. The organic layer was dried over sodium sulfate, filtered, and concentrated in vacuo. The product was treated with hydrogen chloride gas in diethyl ether. Crystallization from ethanol/diethyl ether provided 1.28 g of the desired title product, m.p. =140°–141° C.

Analysis for $C_{19}H_{27}NO_4.HCl$: Calculated: C, 61.70; H, 7.63; N, 3.79; Found: C, 60.14; H, 7.06; N, 3.55.

EXAMPLE 76

4-[4-(Dimethylamino)butoxy]-2-hydroxy-5-allylacetophenone hydrochloride

Following the procedure of Example 75, 1.32 g of the desired title product was recovered when 100 g of dimethylamine were substituted for morpholine, m.p. =88°–90° C.

Analysis for $C_{17}H_{25}NO_3.HCl$: Calculated: C, 62.28; H, 7.99; N, 4.27; Found: C, 61.06; H, 9.19; N, 5.53.

EXAMPLE 77

N-[4-(4-Acetyl-5-hydroxy-2-propylphenoxy)-butyl]acetamide

Approximately 100 milligrams of 4-(4-aminobutoxy)-5-propyl-2-hydroxyacetophenone hydrochloride were treated with acetyl chloride and sodium bicarbonate in acetone. After stirring 48 hours, the mixture was concentrated in vacuo and partitioned between ethyl acetate and saturated sodium chloride solution. The organic layer was separated, washed with dilute hydrochloric acid followed by a saturated potassium carbonate solution, and concentrated to dryness. Preparative thin layer chromatography over silica gel eluting with 1:1 ethyl acetate/hexane provided 10 ml of the desired title product.

Analysis for $C_{17}H_{25}NO_4$: Calculated: C, 66.43; H, 8.20; N, 4.56; Found: C, 65.73; H, 7.60; N, 3.83.

EXAMPLE 78

2-Hydroxy-4-[6-(methylthio)hexyloxy]-5-allylaoetophenone

Ten grams of methane thiol in 25 ml of dimethylformamide were treated with 0.83 g of a 50% sodium hydride dispersion in oil at 0° C. under a nitrogen atmosphere. The reaction was brought to room temperature, and, after stirring two hours, a mixture of 1.5 g of 4-(6-bromohexyloxy)-5-allyl-2-hydroxyacetophenone in 25 ml of dimethylformamide was added. The mixture was heated under a nitrogen atmosphere at 70° C. for 24 hours. After cooling to room temperature, he mixture was partitioned between ethyl acetate and dilute hydrochloric acid. The organic layer was separated, dried over sodium sulfate, and concentrated in vacuo. The residue was purified by preparative thin layer chromatography over silica gel providing 0.73 g of the desired title product, m.p. =42° C.

Analysis for $C_{18}H_{26}O_3S$: Calculated: C, 67.04; H, 8.13; S, 9.94; Found: C, 67.13; H, 8.39; S, 10.16.

EXAMPLES 79 AND 80

2-Hydroxy-4-[6-(methylsulfinyl)hexyloxy]-5-allylacetophenone and
2-hydroxy-4-[6-(methylsulfonyl)-hexyloxy]-5-allylacetophenone A mixture of 0.322 g of 2-hydroxy-4-[6-(methylthio)-hexyloxy]-5-allylacetophenone in 5 ml of methylene chloride was cooled to 0° C. A solution of 0.216 g of 80% meta-chloroperbenzoic acid in 50 ml of methylene chloride was added over a 30 minute period. The reaction mixture was allowed to warm to room temperature and stirred overnight. The reaction mixture was concentrated in vacuo and partitioned between ethyl acetate and a sodium bicarbonate solution. anic layer was separated, dried over sodium sulfate, and concentrated in vacuo. The residue was purified by preparative thin layer chromatography eluting with 1:1 ethyl acetate/hexane providing 30 mg of the title sulfoxide and 70 mg of the title sulfone.

79. 2-Hydroxy-4-[6-(methylsulfinyl)hexyloxy]--allylacetophenone. Analysis for $C_{18}H_{26}O_4S$: Calculated: C, 63.88; H, 7.74; S, 9.47; Found: C, 62.29; H, 7.45; S, 10.42.

80. 2-Hydroxy-4-[6-(methylsulfonyl)hexyloxy]-allylacetophenone.

Analysis for $C_{18}H_{26}O_5S$: Calculated: C, 60.99; H, 7.39; S, 9.05; Found: C, 60.75; H, 7.25; S, 9.17.

EXAMPLES 81-83

The following compounds were prepared from the corresponding bromo derivative according to the procedures of Examples 78-80.

81. 2-Hydroxy-4-[6-(methylthio)hexyloxy]-5-ethylacetophenone, 77.8% yield, m.p. =52°-53° C. NMR.

82. 2-Hydroxy-4-[6-(methylsulfinyl)hexyl-oxy]-5-ethylacetophenone, 17% yield, m.p. =87°-90° C.

Analysis for $C_{17}H_{26}O_4S$: Calculated: C, 62.55; H, 8.03; S, 9.82; Found: C, 62.46; H, 7.78; S, 9.65.

83. 2-Hydroxy-4-[6-(methylsulfonyl)hexyl-oxy]-5-ethylacetophenone, 70% yield, m.p. =124°-126° C.

Analysis for $C_{17}H_{26}O_5S$: Calculated: C, 59.62; H, 7.65; S, 9.36; Found: C, 59.66; H, 7.57; S, 9.42.

EXAMPLE 84

3- -AoetYl-5-hydroxy-2-ethylphenoxy)-methyl]benzoic acid

A mixture of 1.5 g of 3-[(4-acetyl-5-hydroxy-ethyl-phenoxy)methyl]benzonitrile, 1.14 g of potassium hydroxide, 75 ml of ethanol and 75 ml of water was heated at reflux overnight. The mixture was acidified with hydrochloric acid and extracted with ethyl acetate. The organic layer was extracted with 1N sodium hydroxide. The base layer was acidified with hydrochloric acid and extracted with ethyl acetate. The organic layer was dried over sodium sulfate and concentrated in vacuo providing 1.06 g of the desired title product, m.p. =161°-164° C.

Analysis for $C_{18}H_{18}O_5$: Calculated: C, 68.78; H, 5.77; Found: C, 68.62; H, 5.65.

EXAMPLES 85-87

The following acids were prepared from the corresponding nitriles according to the procedure of Example 84.

85. 7-(4-Acetyl-2-ethyl-5-hydroxyphenoxy)heptanoio acid, 89% yield, m.p. =86°-88° C.

Analysis for $C_{17}H_{24}O_5$: Calculated: C, 66.21; H, 7.85; Found: C, 65.31; H, 8.00.

86. 6-(4-Acetyl-2-allyl-5-hydroxyphenoxy)hexanoic acid, 73% yield, m.p. =90°-92° C. NMR.

87. 7-(4-Acetyl-2-ethyl-5-hydroxyphenoxy)-2,2-dimethylheptanoic acid, 28% yield, m.p. =110°-112° C.

Analysis for $C_{19}H_{28}O_5$: Calculated: C, 67.83; H, 8.39; Found: C, 66.68; H, 8.41.

EXAMPLE 88

5-[(4-Cyanobutoxy)-5-ethyl-2-hydroxybenzene]-5-oxopentanoic acid

To a solution of 347 mg of 5-[(4-cyanobutoxy)-5-ethyl-2-hydroxybenzene]-5-oxopentanoic acid, methyl ester in 6 ml of acetone were added 1.5 ml of water followed by 50 mg of lithium hydroxide. After stirring for 1 hour, 2 ml of water were added and the reaction was stirred an additional 3 hours. The solution was concentrated in vacuo, diluted with water to 30 ml, and treated with dilute hydrochloric acid. The resulting precipitate was shaken with ethyl acetate. The organic layer was separated and extracted into a potassium carbonate solution. The potassium carbonate layer was treated with dilute hydrochloric acid and the resulting precipitate was extracted into ethyl acetate. The anic layer was dried over sodium sulfate, filtered, and concentrated in vacuo. The resulting solid was crystallized from diethyl ether providing the 0.19 g of the desired title product, m.p. =140°-142° C.

Analysis for $C_{18}H_{23}NO_5$: Calculated: C, 64.85; H, 6.95; N, 4.20; Found: C, 64.73; H, 7.18; N, 4.46.

EXAMPLES 89-92

The following acids were prepared according to the procedure of Example 88 from the corresponding esters.

89. 2-[4-(4-Cyanobutoxy)-5-ethyl-2-hydroxybenzoyl]benzoic acid, 14% yield, m.p. =162°-166° C.

Analysis for $C_{21}H_{21}NO_5$: Calculated: C, 68.65; H, 5.76; N, 3.81; Found: C, 68.38; H, 5.51; N, 4.10.

90. 6-[(4-Cyanobutoxy)-5-ethyl-2-hydroxybenzene]-6-oxohexanoic acid, 63% yield, m.p. =120°-121° C.

Analysis for $C_{19}H_{25}NO_5$: Calculated: C, 65.69; H, 7.25; N, 4.03; Found: C, 65.70; H, 6.99; N, 3.77.

91. 4[4-(4-Cyanobutoxy)-5-ethyl-2-hydroxybenzoyl]-benzoic acid, 2% yield. NMR.

92. 3-[4-(4-Cyanobutoxy-5-ethyl-2-hydroxybenzoyl]-benzoic acid, 49% yield, m.p. =136°-139° C.

Analysis for $C_{21}H_{21}NO_5$: Calculated: C, 68.65; H, 5.76; N, 3.81; Found: C, 68.87; H, 5.91; N, 3.53.

EXAMPLE 93

3-[(4-Acetyl-3-ethyl-5-hydroxyphenoxy)methyl]-benzoic acid, methyl ester

A mixture of 0.25 g of 3-[-acetyl-2-ethyl-5-hydroxyphenoxy)methyl]benzoic acid, six drops of sulfuric acid, and 50 ml of methanol were heated at reflux ht. The solvent was removed in vacuo and the residue was dissolved in ethyl acetate. The organic solution was washed with base, and concentrated in vacuo. The residue was crystallized from acetone providing 210 mg of the desired title product, m.p. 132.5° C.

Analysis for $C_{19}H_{20}O_5$: Calculated: C, 69.5; H, 6.14; N, 0; Found: C, 68.6; H, 6.18; N, 1.19.

EXAMPLE 94

6-(4-Acetyl-5-hydroxy-2-allylphenoxy)hexanoic acid, methyl ester

The title product was prepared from the corresponding acid following the procedure of Example 93, yield, m.p. =64°-65° C.

Analysis for $C_{18}H_{24}O_5$: Calculated: C, 67.48: H, 7.55: Found: C, 67.08; H, 6.98.

EXAMPLE 95

6-(4-Acetyl-5-hydroxy-2-allylphenoxY)hexanoyl

A mixture of 3.06 g of 6-(4-acetyl-5-hydroxy2-allyl-phenoxy)hexanoic acid, 1.74 ml of oxalyl Chloride, ml of methylene chloride, and ten drops of dimethylformamide was mixed at 0° C. and allowed to warm to room temperature. After stirring for 4 hours, the solvents were removed by evaporation to provide the desired title product. NMR.

EXAMPLE 96

6-(4-Acetyl-5-hydroxy-2-allylphenoxy)hexanamide

Ammonia gas was bubbled into a solution of approximately 3 millimoles of the acid chloride from Example 95 in 25 ml of methylene chloride. After 10 minutes, gas introduction was discontinued and the reaction was stirred overnight. The reaction mixture was concentrated in vacuo and then partitioned between ethyl acetate and dilute hydrochloric acid to which sodium chloride had been added. The organic layer was separated, washed with a potassium carbonate solution, dried over sodium sulfate, and concentrated to dryness. The residue was purified by preparative thin layer chromatography eluting with ethyl acetate to provide 110 mg of the desired title product, m.p. =122°-124° C.

Analysis for $C_{17}H_{23}NO_4$: Calculated: C, 66.86; H, 7.59; N, 4.59; Found: C, 67.13; H, 7.57; N, 4.88.

EXAMPLES 97-100

The following amide derivatives were prepared from the corresponding acid Chloride and the appropriate amine following the procedure of Example 96.

97. 6-(4-Acetyl-5-hydroxy-2-allylphenoxy)-N,N-dimethylhexanamide, 21% yield, m.p. =76° C.

Analysis for $C_{19}H_{27}NO_4$: Calculated: C, 68.44; H, 8.16; N, 4.20; Found C, 69.65; H, 8.39; N, 4.36.

98. 7-(4-Acetyl-2-ethyl-5-hydroxyphenoxy)-N,N-dimethylheptanamide, 48% yield, m.p. =127°-129° C.

Analysis for $C_{19}H_{29}NO_4$: Calculated: C, 68.03; H, 8.71; N, 4.18; Found: C, 67.74; H, 8.70; N, 4.20.

99. 7-( -Acetyl-2-ethyl-5-hydroxyphenoxy)N-methyl-heptanamide, 6% yield, m.p. =55°-57° C.

Analysis for $C_{18}H_{27}NO_4$: Calculated: C, 67.26; H, 8.47; N, 4.36; Found: C, 67.05; H, 8.23; N, 4.21.

100. 6-(4-Acetyl-5-hydroxy-2-allylphenoxy)-droxyhexanamide, 7% yield, m.p. =90°-94° C.

Analysis for $C_{17}H_{23}NO_5$: Calculated: C, 63.54; H, 7.21; N, 4.36; Found: C, 63.69; H, 7.05; N, 4.61.

EXAMPLE 101

7-(4-Acetyl-2-ethyl-5-hydroxyphenoxy)-2,2-methylheptanamide

A mixture of 500 mg of 7-(4-acetyl-2-ethyl-5-hydroxyphenoxy)-2,2-dimethylheptanenitrile in 150 ml of 5N sodium hydroxide and 50 ml of ethanol was heated at reflux overnight. The ethanol was removed by evaporation, 100 ml of water were added, and the solution was extracted with diethyl ether. The organic layer was separated, dried, and concentrated in vacuo. The residue was purified by preparative thin layer chromatography over silica gel eluting with 1:1 ethyl acetate/hexane to provide 34 mg of the desired title product, m.p. =73°-74° C.

Proton nmr and mass spectral analyses were consistent with the structure of the desired product.

EXAMPLES 102 AND 103

7-(4-Acetyl-5-hydroxl-2-allylphenoxy)-2-heptanone and 2-hydroxy-4-(6-hydroxy-6-methylheptyloxy)-5-allylacetophenone A mixture of approximately 5 millimoles of 6(4-acetyl-5-hydroxy-2-allylphenoxy)hexanoyl chloride in 100 ml of d ethyl ether was cooled to −78° C. by means of a dry ice/acetone bath. Under a nitrogen atmosphere, 8.56 ml of a 1.8N solution of methyllithium in diethyl ether was added. The reaction was allowed to warm to −50° C. over a one hour period. The mixture was poured into dilute hydrochloric acid and extracted with ethyl acetate. The organic layer was washed with a saturated sodium Chloride solution, dried over sodium sulfate, and concentrated in vacuo. The residue was purified by preparative thin layer chromatography over silica gel eluting with 40% ethyl acetate in hexane providing 130 mg of the title carbinol and 30 mg of the title ketone.

102. 7-(4-Acetyl-5-hydroxy-2-allylphenoxy -2-heptanone.

Analysis for $C_{18}H_{24}O_4$: Calculated: C, 71.03; H, 7.95; Found: C, 70.75; H, 7.86.

103. 2-Hydroxy-4-(6-hydroxy-6-methylheptyloxy)-5-allylacetophenone.

Analysis for $C_{19}H_{28}O_4$: Calculated: C, 71.22; H, 8.81; Found: C, 70.95; H, 8.95.

EXAMPLE 104

5-(4-Benzoyl-5-hydroxy-2-allylphenoxy)pentanenitrile

A mixture of 0.22 g of 5-(4-benzoyl-5-methoxy-2-allylphenoxy)pentanenitrile, 2.52 ml of a 1M solution of boron tribromide in dichloromethane, and 50 ml of methylene chloride were stirred at −78° C. for two hours. The solution was poured into a cold saturated ammonium chloride solution and ice. The mixture was extracted with ethyl acetate, the organic layer was washed with a cold saturated ammonium chloride solution followed by a saturated sodium chloride solution, dried and concentrated in vacuo. The residue was purified by preparative thin layer chromatography over silica gel eluting with 1:1 ethyl acetate/hexane providing 50 mg of the desired title product, m.p. =60°-62° C. NMR. MS.

EXAMPLES 105-107

The following compounds were prepared from the corresponding methoxy derivatives according to the procedure of Example 104.

105. 5-[5-Hydroxy-4-(1-oxopropyl)-2-allylphenoxy]-pentanenitrile, 4% yield. NMR, MS.

106. 5-[4-(4-Cyanobutoxy)-2-hydroxy-5-allylphenyl)-5-oxopentanoic acid, 11% yield. NMR. MS.

107. 5-[5-Hydroxy-4-(1-oxodecyl)-2-allylphenoxy]-pentanenitrile, 4% yield, m.p. =49°–51° C. NMR, MS.

EXAMPLE 108

5-Ethyl-2-hydroxy-4-[6-methyl-6-(1H-tetrazol5-yl)heptyloxy]acetophenone

A mixture of 317 mg of 7--acetyl-2-ethyl-5-hydroxyphenoxy)-2,2-dimethylheptanenitrile and 996 mg of tributyltinazide was heated at 80° C. for 9 days. After cooling, the reaction mixture was stirred with a few milliliters of methanol for 15 minutes. The mixture was concentrated in vacuo and the residue was purified by high pressure liquid chromatography over silica gel eluting with a 0–70% ethyl acetate in hexane gradient with 0–1% acetic acid added. The appropriate fractions were combined and concentrated in vacuo and the resulting residue was crystallized from methylene chloride/hexane to provide 16 mg of the desired title product, m.p. =160°–162° C. NMR, MS.

EXAMPLE 109

2-Hydroxy-5-allyl-4-[4-(1H-tetrazol-5-yl)-butoxy]acetophenon

A mixture of 8.19 g of 5-(4-acetyl-5-hydroxy2-allylphenoxy)pentanenitrile, 4.86 g of ammonium chloride, and 5.85 g of sodium azide in 50 ml of dimethylformamide was heated at 120° C. overnight. An additional 4.86 g of ammonium chloride and 5.85 g of sodium azide were added and the reaction was stirred an additional 6 hours. The solvent was removed in vacuo and the residue was partitioned between ethyl acetate and dilute cold hydrochloric acid. The organic layer was extracted with a potassium carbonate solution. The aqueous layer was acidified with dilute hydrochloric acid and extracted with ethyl acetate. The organic layer was dried over sodium sulfate, filtered, and concentrated to dryness. Crystallization of the residue from diethyl ether/hexane provided 1.1 g of the desired title product, m.p. =140°–141° C.

Analysis for $C_{16}H_{20}N_4O_3$: Calculated: C, 60.75; H, 6.37; N, 17.71; Found: C, 60.55; H, 6.57; N, 17.61.

EXAMPLE 110

5-Ethyl-2-hydroxy-4-[4-(1H-tetrazol-5-y)butoxy]acetophenone

The title compound was prepared by the procedure of Example 109 from the corresponding nitrile in 29% yield, m.p. =171°–172° C.

Analysis for $C_{15}H_{20}N_4O_3$: Calculated: C, 59.20; H, 6.62; N, 18.41; Found: C, 58.95; H, 6.35; N, 18.44.

EXAMPLE 111

5,5'-[(4-Acetyl-6-methoxymethyl-1.3-phenylene)bis(oxy)]bis pentanenitrile]

A mixture of 688 mg of 5,5'-[(4-acetyl-6-hydroxymethyl-1,3-phenylene)bis(oxy)]bis pentanenitrile]in 15 ml of dimethylformamide was added to a suspension of 0.184 of a 50% oil dispersion of sodium hydride and 0.62 ml of methyl iodide in 45 ml of dimethylformamide at 0° C. The reaction was allowed to come to room temperature and stirred overnight. The reaction mixture was partitioned between ethyl acetate and dilute hydrochloric acid to which sodium chloride had been added. The organic layer was separated, dried over sodium sulfate, and concentrated in vacuo. The resulting residue was purified by high pressure liquid chromatography over silica gel eluting with a 0–70% ethyl acetate in hexane gradient to provide 110 mg of the desired title product. NMR, MS.

EXAMPLE 112

7-(4-Acetyl-5-methoxy-2-methoxymethylphenoxy)-heptanenitrile

The title product was prepared in 25.1% yield from the corresponding hydroxymethyl analog according to the procedure of Example 111. NMR.

EXAMPLE 113

5-(4-Acetyl-5-methoxy-2-allyphenoxy)pentane

A mixture of 1.365 g of 5-(4-acetyl-5-hydroxy 0.966 g of potassium carbonate, and 1.42 g of methyl iodide in 50 ml of dimethylformamide was stirred together at room temperature for 5 hours. The mixture was partitioned between dilute hydrochloric acid and ethyl acetate. The organic layer was separated, dried over sodium sulfate, and concentrated in vacuo to provide 1.2 g of the desired title product, m.p. =40°–42° C. NMR, MS.

EXAMPLE 114

3-(4-Acetyl-2-ethyl-5-methoxyphenoxy)methyl]-benzonitrile

The title compound was prepared in 30% yield from the compound of Example 55 and methyl iodide according to the procedure of Example 16, m.p. 124°–126° C.

Analysis for $C_{19}H_{19}NO_3$: Calculated: C, 73.77; H, 6.19; N, 4.53; Found: C, 73.51; H, 6.22; N, 4.51.

EXAMPLE 115

5-(4-Acetyl-5-methoxy-2-allylphenoxy)pentanenitrile

The title compound was prepared in 14% yield from the corresponding phenol according to the procedure of Example 111, m.p. =41°–42° C.

Analysis for $C_{17}H_{21}NO_3$: Calculated: C, 71.06; H, 7.37; N, 4.87; Found: C, 70.89; H, 7.17; N, 4.83.

EXAMPLE 116

15 2-Hydroxy-5-propyl-4-[4-(1-tetrazol-5-yl)-butoxy]acetophenone

One gram of 2-hydroxy-5-allyl-4-[4-(1H-tetrazol-5-yl)butoxy]acetophenone was hydrogenated in the presence of 0.5 g of 5% palladium on carbon in 50 ml of ethanol for 1 hour. The reaction mixture was filtered and concentrated in vacuo. The residue was crystallized from diethyl ether to provide 0.7 g of the desired title product, m.p. =135°–136° C.

Analysis for $C_{16}H_{22}N_4O_3$: Calculated: C, 60.36; H, 6.97; N, 17.60; Found; C, 60.65; H, 7 12; N, 17.46.

EXAMPLES 117 AND 118

The following compounds were prepared according to the procedure of Example 116 from the corresponding allyl derivatives.

117. 6-(4-Acetyl-5-hydroxy-2-propylphenoxy)hexanoic acid, 60% yield, m.p. =90°–92° C.

Analysis for $C_{17}H_{22}O_5$: Calculated: C, 66.65; H, 7.24; Found: C, 66.48; H, 7.29.

118. 5-(4-Acetyl-5-hydroxy-2-propylphenoxy)-pentanenitrile, 77% yield. m.p. =64°-66° C.

Analysis for $C_{16}H_{21}NO_3$: Calculated: C, 69.79; H, 7.69; N, 5.09; Found: C, 70.00; H, 7.56; N, 5.27.

EXAMPLES 119-120

2-Hydroxy-4-[4-(1-methyl-1H-tetrazol-5-yl)-butoxy]-5-allylacetophenone and
2-hydroxy-4-[2-methyl-2H-tetrazol-5-yl)butoxy]-5-allylacetophenone A mixture of 632 mg of 2-hydroxy-4-[4-(1Htetrazol-5-yl)butoxy]-5-allylacetophenone, 0.29 ml of methyl iodide, 0.29 g of potassium carbonate and ml of dimethylformamide were allowed to react overnight. The mixture was then heated to 50° C. under a en atmosphere for 4 hours, Cooled, and partitioned between dilute hydrochloric acid and ethyl acetate The organic layer was separated, dried over sodium sulfate, and concentrated in vacuo. The residue was purified by preparative thin layer chromatography over silica gel eluting with 100% ethyl acetate providing mg of the title 1-methyl derivative and 100 mg of the desired 2-methyl compound.

119. 2-Hydroxy-4-[4-(1-methyl-1H-tetrazol-yl)butoxy]-5-allylacetophenone, m.p. =38°-40° C.

Analysis for $C_{17}H_{22}N_4O_3$: Calculated: C, 61.80; H, 6.71; N, 16.74; Found: C, 61.53; H, 6.99; N, 16.74.

120. 2-Hydroxy-4-[4-(2-methyl-2H-tetrazol5-yl)butoxy]-5-allylacetophenone, m.p. =80°-81° C.

Analysis for $C_{17}H_{22}N_4O_3$: Calculated: C, 61.80; H, 6.71; N, 16.96; Found: C, 62.05; H, 6.97; N, 16.77.

EXAMPLES 121-125

The following compounds were prepared according to the procedure of Examples 119-120 from the corresponding tetrazole derivative.

121. 2-Hydroxy-4-3-(2-methyl-2H-tetrazol-5-yl)phenyl]methoxy}-5-allylacetophenone, 10% yield.

122. 2-Hydroxy-4-[4-(1-methyl-1H-tetrazol-5-yl)butoxy]-5-ethylacetophenone, 38% yield, m.p. =90°-91° C.

Analysis for $C_{16}H_{22}N_4O_3$: Calculated: C, 60.36; H, 6.97; N, 17.60; Found: C, 60.69; H, 7.25; N, 17.27.

123. 2-Hydroxy-4-[4-(2-methyl-2H-tetrazol-5-yl)butoxy]-5-ethylacetophenone, 27% yield, m.p. =65°-66° C.

Analysis for $C_{16}H_{22}N_4O_3$: Calculated: C, 60.36; H, 6.97; N, 17.60; Found: C, 60.53; H, 6.59; N, 17.43.

EXAMPLE 124

5,5'-{[4-Acetyl-6-(hydroxymethyl)-1,3-phenylene]bis(oxy)bispentanenitrile]

Two grams of 5,5'-{[4-acetyl-6-formyl-1,3-phenylene]bis(oxy)}bis[pentanenitrile]were hydrogenated in the presence of 1 g of 10% palladium on Carbon in ml of ethanol. The reaction mixture was filtered, concentrated in vacuo and triturated with diethyl ether to provide 1.6 g of the desired product, m.p. =98°-99° C.

Analysis for $C_{19}H_{24}N_2O_4$: Calculated: C, 66.26; H, 7.02; N, 8.13; Found: C, 65.96; H, 6.76; N, 8.01.

EXAMPLE 125

5-[4-Acetyl-5-hydroxy-2-(2-hydroxypropyl)-phenoxy]-pentanenitrile

A. Preparation of 5-[4-acetyl-5-hydroxy-2-(2,3-epoxypropyl)phenoxy]-pentanenitrile.

To a solution of 5.46 g of 5-[4-acetyl-5-hydroxy-2-allylphenoxy pentanenitrile in 100 ml of methylene chloride were added 6.1 g of 85% meta-chloroperbenzoic acid. After stirring for 5 hours, the reaction mixture was concentrated in vacuo. The residue was partitioned between ethyl acetate and a cold sodium carbonate solution. The organic layer was separated, dried over sodium sulfate, and concentrated in vacuo to approximately 35 ml. The solution was placed in a freezer overnight providing 4.08 g of the crystalline the product which were recovered by filtration, m.p. 86°-87° C.

B Preparation of 5-[4-acetyl-5-hydroxy-2-(2-hydroxypropyl)phenoxy]-pentanenitrile.

The epoxide intermediate from Example 125A above (0.9 was hydrogenated in the presence of 0.5 g of 5% palladium on carbon in 50 ml of ethanol. Filtration of the reaction mixture and crystallization from diethyl ether provided 190 mg of the desired title product, m.p. =86°-88° C.

Analysis for $C_{16}H_{21}NO_4$: Calculated: C, 65.96; H, 7.27; N, 4.81; Found: C, 65.79; H, 4.32; N, 4.56.

EXAMPLE 126

5,5'-{[[4-Acetyl-6-(chloromethyl)-1,3-phenylene]bis(oxy)]bis[pentanenitrile]

The compound of Example 124 (688 mq) was dissolved in 50 ml of dimethylformamide. To this solution were added 0.29 ml of collidine followed by 0.252 g of lithium chloride. The reaction was cooled by means of an external ice bath and 0.507 ml of methane sulfonyl chloride were added. After stirring for 2 hours, the reaction was allowed to warm to room temperature. The mixture was poured into cold dilute hydrochloric acid to which sodium chloride had been added and the solution was extracted with ethyl acetate. The organic layer was washed twice with cold hydrochloric acid/sodium chloride, dried over sodium sulfate, and concentrated in vacuo. Concentration of the solution provided a residue which was crystallized from methylene chloride/hexane to provide 180 mg of the desired title product, m.p. =110°-110° C. (decomposition).

Analysis for $C_{19}H_{23}ClN_2O_3$: Calculated: C, 67.02; H, 7.31; N, 7.82; Found: C, 67.02; H, 7.04; N, 7.73.

EXAMPLE 127

7-[4-Acetyl-5-hydroxy-2-(chloromethyl)phenoxy]-heptanenitrile

The title product was prepared in 70% yield from the corresponding hydroxymethyl compound according to the procedure of Example 126. NMR.

EXAMPLE 128

7-[4-Acetyl-5-hydroxy-2-(methylthiomethyl)-phenoxy]heptanenitrile

A mixture of 600 mg of the compound from Example 127 was dissolved in 50 ml of methylene chloride and cooled to 0° C. Fifteen grams of methanethiol were added followed by the addition of 2 ml of triethylamine. The reaction was allowed to warm to room temperature and was stirred overnight. The reaction mixture was concentrated in vacuo and partitioned between ethyl acetate and an acidic sodium chloride solution. The organic layer was separated, dried over sodium sulfate, and concentrated in vacuo. The residue was purified by preparative thin layer chromatography over silica gel eluting with 40% ethyl acetate in hexane providing 200 mg of the desired title product, m.p. =78° C.

Analysis for $C_{17}H_{23}NO_3S$: Calculated: C, 63.52; H, 7.21; N, 4.36; S, 9.98; Found: C, 63.64; H, 6.98; N, 4.60; S, 9.71.

EXAMPLE 129

7-[4-Acetyl-5-hydroxy-2-(methoxymethyl)phenoxy]-hdptanentrile

Approximately 3 millimoles of the chloro compound of Example 127 were treated with 0.624 g of silver perchlorate in 50 ml of methanol at 0° C. The reaction mixture was allowed to warm to room temperature over a 2 hour period. The mixture was then partitioned between ethyl acetate and an acidic sodium chloride solution. The organic layer was separated, dried over sodium sulfate, filtered, and concentrated in vacuo. The residue was purified by preparative thin layer chromatography over silica gel eluting with 1:1 ethyl acetate/hexane providing 50 mg of the title compound. NMR, MS.

EXAMPLE 130

5-(4-Benzoyl-2-ethyl-5-hydroxyphenoxy)pentanenitrile

Following the procedure of Example 16, 0.726 g of 5-ethyl-2,4-dihydroxybenzophenone and 0.53 g of 5-bromopentanenitrile were allowed to react and provided 0.37 g of the desired title product, m.p. =42°–44° C.

Analysis for $C_{20}H_{21}NO_3$: Calculated C, 74.28; H, 6.55; N, 4.33; found: C, 74.14; H, 6.62; N, 4.51

EXAMPLE 131

5-(4-Acetyl-5-hydroxy-2-allylphenoxy)pentanoic acid

When 2 g of 5-(4-acetyl-5-hydroxy-2-allylphenoxy)pentanenitrile were hydrolyzed following the procedure of Example 84, 198 g of the desired title product were recovered, m.p. =110°–111° C.

Analysis for $C_{16}H_{20}O_5$: Calculated: C, 65.97; H, 6.57; Found: C, 65.86; H, 6.181

EXAMPLE 132

5-(4-Acetyl-5-hydroxy-2-propylphenoxy)pentanoic acid

The compound of Example 131 (1.46 g) was added to 150 ml of ethanol and hydrogenated in the presence of 1.5 g of 5% palladium on carbon. After the theoretical amount of hydrogen was taken up, the reaction wad discontinued, the reaction mixture was filtered. The filtrate was concentrated in vacuo and provided 1.49 g of the desired title product, m.p. =106° C.

Analysis for $C_{16}H_{22}O_5$: Calculated: C, 65.51; H 7.22; Found: C, 66.77; H, 8.12

EXAMPLE 133

5-(4-Acetyl-2ethyl-5-hydroxyphenoxy)-2,2-dimethylpentanenitrile

Following the procedure of Example 68, 4.52 g of 4-(3-bromopropoxy)-5-ethyl-2-hydroxyacetophenone and 1.36 ml of isobutyronitrile were reacted to provide 1.72 g of the desired title compound, m.p. =55°–56° C.

Analysis for $C_{17}H_{23}NO_3$: Calculated: C, 70.56; H, 8.01; N, 4.84; Found: C, 69.19; H, 8.05; N, 4.33.

EXAMPLES 134–135

5-(4-Acetyl-2-ethyl-5hydroxyphenoxy)-2,2-dimethylpentanoic acid and
5-(4-acetyl-2ethyl-5-hydroxyphenoxy)-2,2-dimethylpentanamide Following the procedure of Example 84, 114 mg of the nitrile of Example 133, 15 ml of 5N sodium hydroxide, and 50 ml of ethanol were heated at reflux for 24 hours. After workup, purification by preparative thin layer chromatography over silica gel provided 11 mg of the title amide and 13 mg of the title acid.

134. 5-(4-Acetyl-2ethyl-5-hydroxyphenoxy)-2,2-dimethylpentanoic acid, m.p. =128°–131° C.

Analysis for $C_{17}H_{24}O_5$: Calculated: C. 66.21; H, 7.85; N, O; Found: C, 63.14; H, 7.55; N, 0.60.

135. 5-(4-Acetyl-2-ethyl-5-hydroxyphenoxy)-2,2-dimethylpentamide, m.p. =104°–105° C.

Analysis for $C_{17}H_{25}NO_4$: Calculated: C, 66.43; H, 8.20; N, 4.56; Found: C, 65.76; H, 8.57; N, 3.97.

EXAMPLE 136

1-(5-Ethyl-2-hydroxy-4-{[4-methyl-4-(1H-tetrazol-5-yl)pentyl]oxy}phenyl)ethanone The title tetrazole was prepared in 48% yield from the nitrile from Example 133 according to the procedure provided in Example 108, m.p. =156°–157° C.

Analysis for $C_{17}H_{24}N_4O_3$: Calculated: C, 61.43; H, 7.28; N, 16.86; Found: C, 61.60; H, 7.02; N, 16.80.

EXAMPLE 137

1-{4-[(5-Aminopentyl)oxy]-5-ethyl-2-hydroxyphenyl}ethanone

A mixture of 2.0 g of 5-(4-acetyl-2-ethyl-5-hydroxyphenoxy)pentanenitrile, 50 ml of acetic acid, and 2.0 g of 10% palladium on carbon were subjected to hydrogenation for approximately 2 hours. The mixture was then filtered and concentrated in vacuo. The residue was triturated with diethyl ether to provide 2 g of the desired title product, m.p. =75°–76° C. NMR.

EXAMPLE 138

N-[5-(4-Acetyl-2-ethyl-5-hydroxyphenoxy)-pentyl]acetamide

In a manner analogous to that taught in Example 77, 265 mg of the amine from Example 137 was acylated with acetyl chloride and pyridine to provide 158 mg of the desired title product, m.p. =115°–116° C.

Analysis for $C_{17}H_{25}NO_4$: Calculated: C, 66.43; H, 8.20; N, 4.56; Found: C, 66.24; H, 8.29; N, 4.47

EXAMPLE 139

5-(4-Acetyl-5-hydroxy-2-allylphenoxy)pentanenitrile

The title product was prepared in 88% yield from 5-allyl-2,4dihydroxyacetophenone and 5-bromopentanenitrile following the procedure of Example 16, m.p. =54° C.

Analysis for $C_{16}H_{19}NO_3$: Calculated: C, 70.31; H, 7.01; N, 5.12; Found: C, 69.38; H, 7.54; N, 4.80.

EXAMPLE 140

1-(5-Ethyl-2-hydroxy-4-{[6-(1H-tetrazol-5-yl)-hexyl]oxy}phenyl)ethanone

The title compound was prepared in 63% yield from the nitrile of Example 20 following the procedure of Example 108, m.p. =126°-127° C.

Analysis for $C_{17}H_{24}N_4O_3$: Calculated: C, 41.43; H, 7.28; N, 16.86; Found: C, 71.47; H, 7.11; N, 16.88.

EXAMPLES 141-142

5-[4-(4-Acetyl-2-ethyl-5-hydroxyphenoxy)-butyl]-2H-tetrazole-2-acetic acid, ethyl ester and
5-[4-(4-acetyl-2-ethyl-5-hydroxyphenoxy)butyl]-1H-tetrazole-1-acetic acid, ethyl ester The title products were prepared by the method provided in Examples 119-120 employing 2-hydroxy-4-[4-(1H-tetrazol-5-yl) butoxy]-5-ethylacetophenone and ethyl bromoacetate.

141. 5-[4-(4-(4-Acetyl-2ethyl-5-hydroxy-phenoxy)-butyl)-2H-tetrazole-2-acetic acid, ethyl ester, 29% yield m.p. =118°-121° C.

Analysis for $C_{19}H_{26}N_4O_5$: Calculated: C, 58.44; H, 6.71; N, 14.35; Found: C, 58.15; H, 6.56; N, 14.52.

142. 5-[4-(4-Acetyl-2ethyl-5-hydroxyphenoxy)-butyl]-1H-tetrazole-1-acetic acid, ethyl ester, 18% yield, m.p. =86°-87° c.

Analysis for $C_{19}H_{26}N_4O_5$: Calculated: C, 58.44; H, 6.71; Found: C, 58.66; H, 6.89.

EXAMPLES 143-144

The following acid derivatives were prepared from the corresponding esters of Examples 141-142 upon hydrolysis in aqueous ethanol with potassium hydroxide.

143. 5-[4-(4-Acetyl-2ethyl-5-hydroxyphenoxy)-butyl]-2H-tetrazole-2-acetic acid, 80% yield, m.p. >230° C. NMR. MS.

144. 5-[4-(4-Acetyl-2-ethyl-5-hydroxyphenoxy)-butyl]-1H-tetrazole-1-acetic acid, 80% yield, m.p. =161°-162° C.

Analysis for $C_{17}H_{22}N_4O_5$: Calculated: C, 56.35; H, 6.12; N, 15.47; Found: C, 56.62; H, 6.30; N, 15.25.

EXAMPLE 145

7-(4-Acetyl-2-ethyl-5-hydroxyphenoxy)-N-1H-tetrazol-5-ylheptanamide

The acid chloride of 616 mg of 7-(4-acetyl-5-hydroxy-2-ethylphenoxy)heptanoic acid was prepared according to the procedure of Example 95. To the acid chloride were added 2.06 g of 5-aminotetrazole hydrate, 16.4 g of sodium bicarbonate, and 100 ml of acetone. The reaction was stirred for 2 days. The solvent was removed in vacuo and the residue was partitioned between ethyl acetate and water. The water layer was separated and acidified with hydrochloric acid and extracted with ethyl acetate. The organic layer was separated, dried over sodium sulfate, filtered, and concentrated in vacuo. Crystallization of the residue from methanol/water provided 76 mg of the desired product, m.p. =196°-200° C.

Analysis for $C_{18}H_{25}N_5O_4$: Calculated: C, 57.59; H, 6.71; N, 18.65; Found: C, 57.42; H, 6.60; N, 18.38.

EXAMPLE 146

1-(5-Ethyl-2-hydroxy-4-{[5-(1H-1,2,4-triazol-1-yl) pentyloxy}phenyl)ethanone

A mixture of 0.3 g of 5-(4-acetyl-2-ethyl-5-hydroxyphenoxy)pentyl bromide, 0.06 g of triazole, and 0.13 g of potassium carbonate in dimethylformamide was heated at 80°-90° C. for approximately 18 hours. The mixture was poured into acidic water and extracted with ethyl acetate and methylene chloride. The extracts were combined, washed with dilute sodium hydroxide solution, dried over sodium sulfate, and concentrated in vacuo. The residue was twice crystallized from ethyl acetate/hexane to provide the title product having a melting point of 87° C.

Analysis for $C_{17}H_{23}N_3O_3$: Calculated: C, 64.33; H, 7.30; N, 13.24; Found: C, 64.07; H, 7.23; N, 13.06.

EXAMPLE 147

4-[(4-Acetyl-2-ethyl-5-hydroxyphenoxy)methyl]-2-hydroxybenzoic acid, ethyl ester A mixture of 0.75 g of 2,4-dihydroxy-5-ethylacetophenone, 1.23 g of ethyl 2-acetoxy-4-bromomethylbenzoate, 0.57 g of potassium carbonate, and a catalytic amount of potassium iodide were heated at reflux in methyl ethyl ketone overnight. The hot mixture was filtered and the filtrate concentrated to dryness. Crystallization of the residue from ethyl acetate/hexane provided 130 mg of the desired title product, m.p. 145°-146° C.

Analysis for $C_{20}H_{22}O_6$: Calculated: C, 67.02; H, 6.18; Found: C, 68.16; H, 6.15.

EXAMPLE 148

4-[(4-Acetyl-2-ethyl-5-hydroxyphenoxy)methyl]-2-hydroxybenzoic acid

The title product was prepared in 69% yield from the corresponding ethyl ester upon heating with potassium hydroxide in aqueous ethanol, m.p. 214°-216° C.

Analysis for $C_{18}H_{18}O_6$: Calculated: C, 65.45; H, 5.49; Found: C, 65.67; H, 5.60.

EXAMPLE 149-150

In a manner analogous to the procedure of Example 96, the following compounds were prepared from the corresponding acid chlorides in a solution of methylene chloride upon treatment with N-methylhydroxylamine hydrochloride in the presence of triethylamine and tetrahydrofuran.

149. 7-(4-Acetyl-2-ethyl-5-hydroxyphenoxy)-N-hydorxy-N,2,2-trimethylheptanamide, 45% yield from the acid Analysis for $C_{20}H_{31}O_5$: Calculated: C, 65.73; H, 8.55; N, 3.83; Found: C, 65.94; H, 8.76; N, 3.58.

150. N-Methyl-N-hydroxy-9-(4-acetyl-2-ethyl-5-hydroxyphenoxy)-2,2-dimethylnonanamide, 17% yield from the acid Analysis for $C_{22}H_{35}O_5$: Calculated: C, 67.14; H, 8.97; N, 3.56; Found: C, 66.96; H, 8.89; N, 3.81.

EXAMPLE 151

2,4-Diethyl-5-{[6-methyl-6-(1H-tetrazol-5-yl)heptyl]oxy}phenol

To a solution of 1 gram of 5-ethyl-2-hydroxy-4-[6-methyl-6-(1H-tetrazol-5-yl) heptyloxy]acetophenone in 25 ml of acetic acid were added 25 ml of hydrochloric acid and 0.73 grams of zinc in portions over 15 minutes. The mixture was stirred overnight, filtered, and the filtrate partitioned between ethyl acetate and a saturated sodium chloride solution. The organic layer was dried over sodium sulfate, filtered, and concentrated in vacuo. The residue was purified by high pressure chromatography over silica gel eluting with 1:1 ethyl acetate/hexane with one percent acetic acid. The appropriate fractions were combined and concentrated in vacuo to provide 318 mg of the desired titled product as an oil.

Analysis for $C_{19}H_{30}N_4O_2$: Calculated: C, 65.87; H, 8.73; N, 16.17; Found: C, 65.62; H, 8.70 N, 15.93.

EXAMPLE 152

7-{4-[-(Hydroxyimino)ethyl]-2-ethyl-5-hydroxyphenoxy}-2,2-dimethylheptanoic acid A mixture of 7.1 g of 7-(4-acetyl-2-ethyl-5-hydroxyphenoxy)-2,2-dimethylheptanoic acid, 0.149 g of hydroxylamine hydrochloride, 0.176 g of sodium acetate, and 50 ml of methanol were heated at reflux for 48 hours. The reaction mixture was allowed to cool to room temperature and the resulting solid collected by filtration. The solid was crystallized from methylene chloride/hexane to provide 0.32 g of the desired titled product.

Analysis for $C_{19}H_{29}NO_5$: Calculated: C, 64.93; H, 8.31; N, 3.99; Found: C, 65.50; H, 8.42; N, 4.89.

The compounds of this invention have demonstrated activity in vivo in various test systems designed to detect effective antiinflammatory agents. These pharmacodynamic effects were demonstrated in the following test systems.

Carrageenin Assay

The compounds were evaluated for antiinflammatory activity in the test method described by C. A. Winter, *Proc. Soc. Exp. Biol. Med.*, 111, 544 (1962). In this test, inflammation is created by injecting carrageenin into the hind paws of rats. Test compounds are administered prior to injection to determine percent inhibition of the subsequent inflammation in comparison with control animals. The results are reported in Table I.

TABLE I

Antiinflammatory Activity in the Carrageenin Assay

| Compound of Example No. | Percent Inhibition |
|---|---|
| 19 | 26% |
| 20 | 19% |
| 47 | 53–65% |
| 48 | 30% |
| 49 | 43% |
| 50 | 50–82% |
| 51 | 79% |
| 53 | 50–60% |
| 55 | 70% |
| 68 | 33% |
| 82 | 31% |
| 83 | 26% |
| 87 | 15% |
| 100 | 38% |
| 108 | 61% |
| 110 | 64% |
| 122 | 53% |
| 123 | 55% |
| 136 | 41% |
| 140 | 31% |

*Compounds administered at a dose of 50 mg/kg i.p.

Arachidonic Acid-Induced Ear Edema Assay

Female BALB/C mice (Charles River; 18–20 rams) were divided into groups of five. Arachidonic acid was dissolved in ethanol at a concentration of 200 mg/ml. Each mouse received 2 mg/ear of arachidonic acid on the inner surface of the right ear. This dose of phlogistic was applied by an automatic pipette in 10 mcl volumes. The left ear (control) received ethanol. Drugs were applied topically in an ethanol-based gel to the entire outer surface of both ears one hour prior to arachidonic acid application. Edema was measured by the increase in ear weight. An hour after arachidonic acid solution or vehicle was applied, an ear sample of 7 mm in diameter was obtained from both ears. Ear edema was calculated by subtracting the weight of the right ear sample (treated ear) from left ear (control), dividing by the weight of the left/Control ear, and averaging the results for each group of mice according to compound and concentration. The results are reported below in Table II.

TABLE II

Inhibition of Arachidonic Acid Induced Ear Edema

| Compound of Example No. | Dose* | Percent Inhibition of Ear Swelling |
|---|---|---|
| 20 | 1% | |
| 47 | 0.05% | 52 |
| 48 | 0.05% | 13.6 |
| 49 | 0.05% | 31 |
| 50 | 0.05% | 29–47 |
| 51 | 0.05% | 43 |
| | 0.1% | 31 |
| 53 | 0.05% | 24 |
| 55 | 0.05% | 43–59 |
| | 1% | 57 |
| 56 | 0.05% | 6 |
| 59 | 0.05% | 0 |
| 68 | 1% | 46 |
| 78 | 1% | 46 |
| 82 | 1% | 9 |
| 83 | 0.028% | 59 |
| 87 | 1% | 3 |
| 98 | 1% | 17 |
| 100 | 1% | 18 |
| 108 | 1% | 60 |
| 110 | 1% | 58 |
| 114 | 0.05% | 40 |
| | 0.01% | 44 |
| 121 | 0.05% | 0 |
| 122 | 1% | 10 |
| 123 | 1% | 58 |

*concentration of compound in ethanol gel

Anti IL-1 Activity [Thymocyte Assay]

Thymus from 3–4 week old C3H/HeJ male mice and were passed through a #100 mesh screen to make a single cell suspension. The cells were suspended in RPMI-1640 supplemented with $2 \times 10^{-5}$M 2-mercaptoethanol, 3% fetal calf serum, and 1% Penicillin/Streptomycin. The cell suspension was placed in a tissue culture flask and incubated at 37° C. in 5% carbon dioxide in air for 1-2 hours. The thymocytes were decanted, leaving adherent cells behind, and the liquid was centrifuged at 1400 rpm for 10 minutes. After decanting the supernatant, the cells were resuspended and counted with a hemocytometer. The density was adjusted to 2×7 cells/ml. Fifty µl of the suspension were added to each well of a 96-well microtiter plate, followed by the addition of 25 µl of PHA and 25 µl IL-1 (1:25 dilution of a 10 mcg/ml stock solution) per well.

Each compound to be tested was dissolved in 30% DMSO/70% PBS to make a stock solution of 1 mg/ml. Fifteen µl of each compound were added to 300 µl of media in the serial dilution plate. Twenty-five µl of each drug were added to the test plate in quadruplicate wells across the plate. The plate was incubated at 37° C. in 5% carbon dioxide in air for 48 hours. The wells were pulsed with tritiated thymidine (5 µCi.well) for 4 hours before harvesting on a Skatron cell harvester. The filter discs were placed in mini-vials, scintillation fluid (Tol-Pop) was added, and the vials counted. The percent of counts for each vial compared with control samples wherein no compound was added (vehicles only) was determined for each compound and are reported as Table III below as the percent T-cel suppression.

TABLE III

| Suppression of IL-1 induced T-cell Proliferation | | |
|---|---|---|
| Compound of | Percent T-cell suppression | |
| Example | 10 mcg/ml | 1 mcg/ml |
| 15 | 91 | 33 |
| 20 | 99 | 39 |
| 30 | 91 | 32 |
| 36 | 75 | 15 |
| 38 | 28 | −8 |
| 68 | 99 | 13 |
| 76 | 79 | 39 |
| 82 | 88 | 21 |
| 83 | 43 | 29 |
| 89 | 39 | 9 |
| 90 | 47 | 3 |
| 92 | 38 | 5 |
| 98 | 85 | 14 |
| 107 | 26 | 47 |
| 109 | 56 | 7 |
| 115 | 96 | 29 |
| 122 | 87 | 37 |
| 123 | 90 | 36 |
| 125 | 85 | 30 |
| 130 | 99 | 41 |
| 132 | 59 | 15 |

Mouse Endotoxin Shock Assay

Compounds were given to 18-20 g C57BL/6 male mice using various regimens depending upon mode of administration. Control animals received corresponding vehicles only. The mice were then challenged with 0.2 ml of chromatographically purified 0111:B4 E. coli LPS and galactosamine hydrochloride (GALN) given subcutaneously (back of the neck). GALN was given at an approximate dose of 500 mg/kg whereas the LPS dose ranged between 0.3-1.2 µg/mouse (15-60 µg/k9). Control animals generally die of shock 7-15 hours after administration of LPS/GALN although a small number (0-5%) may die 24-48 hours after such administration. Calculation of the EDso for each compound was performed using the Reed Muench Method for results obtained 48 hours after challenge. Results are summarized in Table IV below.

TABLE IV

| Mouse Endotoxin Shock Assay | |
|---|---|
| Compound of Example No. | $ED_{50}$ (mg/kg) |
| 47 | 24 |
| 48 | 18.6 |
| 49 | >50 |
| 50 | 9.5 |
| 51 | 27 |
| 54 | 21 |
| 55 | 3.1 |
| 68 | >50 |
| 82 | >50 |
| 83 | >50 |
| 93 | 25 |
| 108 | >50 |
| 122 | 42 |

The compounds of Formula I should be useful in treating any condition, including clinical conditions, which is characterized by the excessive release of leukotriene $B_4$. These conditions include psoriasis, arthritis, chronic lung diseases, inflammatory bowel disease, and other inflammatory states characterized by the infiltration and aggregation of polymorphonuclear leukooytes.

The term "excessive release" of leukotriene $B_4$ refers to an amount of leukotriene sufficient to cause the particular condition associated with such amount. The amount of $LTB_4$ which is considered to be excessive will depend on a variety of factors, including the amount of leukotriene required to cause the particular condition, and the species of the mammal involved. As will be appreciated by those skilled in the art, the success of treating a mammal suffering from or susceptible to a condition characterized by an excessive release of leukotriene $B_4$ with a compound of formula I will be measured by the regression or prevention of the symptoms of the condition.

Leukotriene $B_4$ antagonism was demonstrated by the following test procedure:

Inhibition of Binding of $^3H$-$LTB_4$ to Peripheral Human Neutrophils

The effectiveness of compounds to inhibit the binding of leukotriene $B_4$ to a specific receptor on the membrane of human neutrophils was measured by using an adaptation of a radio-ligand binding assay developed by Goldman and Goetzl, J. Immunol., 129, 1600 (1982). Other investigators have developed similar assays (see, e.g., Kreisle, et al., J. Exp. Med., 157, 628 (1983) and Lin, et al., Prostaglandins, 28, 837 (1984)).

Cells used in the assay were isolated by standard techniques of centrifugation on Ficol-Hypaque, dextran 70 sedimentation and hypotonic lysis. The following procedure was used. Freshly-prepared buffy coat layers from two individuals were obtained from a local blood donor center. The cells were mixed and diluted to 484 ml. with phosphate buffered saline containing heparin (10 units/ml) and heat-inactivated calf serum (5%). This was divided into 20 ml. aliquots and the aliquots layered on top of Ficoll-Paque (12 ml.). The material was then centrifuged at 500 g. for 40 minutes at room temperature. The resulting upper layer of platelets and mononuclear cells was discarded. The lower layer containing erythrocytes and neutrophils was retained. Buffer was added (1 ml. per 4 ml. of lower layer) and the suspension mixed. For each milliliter of this mixture, 0.33 ml. of 6% Macrodex was added. After stirring, the cels were allowed to sediment for 1 hour at 37° C. The resulting erythrocyte pellet was discarded and the neutrophil enriched supernatant fluid centrifuged at 500 g. for 10 minutes at 4° C. Erythrocytes still present in this cell pellet were lysed by incubating the cells with 5-8 ml. ice-cold distilled water for 30-45 seconds. Subsequently, the volume was made up to 50 ml. by addition of ice-cold buffer and the cells resuspended. The suspension was then centrifuged at 300 g. for 10 minutes at 4° C. The cells were finally resuspended at a cell density of $2 \times 10^7$ cells/ml in the assay buffer. This buffer Consisted of Hanks' balanced salt solution and 0.1% ovalbumin (pH 7.3). This isolation procedure resulted in cell preparations of $\geq 90\%$ neutrophils and $\geq 90\%$ viability.

The radio-ligand binding assay was conducted by incubating neutrophils ($1 \times 10^7$ cells) with 0.1–0.2 nM $^3$H-LTB$_4$ (sp. act. 150-220 Curies/mmol) and test compound ($1 \times 10^{-5}$M and $1 \times 10^{-6}$M) for 10 minutes at 4° C. The amount of bound $^3$H-LTB$_4$ was then measured and compared with the amount bound in the absence of test compound. The assay was carried out in microcentrifuge tubes by adding first 10 μl test compound dissolved in DMSO, followed by adding 20 μl $^3$H-LTB$_4$ diluted in assay buffer, and finally adding 500 μl of the cell suspension pension. At the end of the 10 minutes incubation, 300 μl of a mixture of dibutyl and dinonyl phthalate (7:2) were added and the tubes centrifuged for 2 minutes in a microcentrifuge. The radioactivity bound to the cell pellet was measured by scintillation spectroscopy. Appropriate corrections for nonspecific bonding of $^3$H-LTB$_4$ were made. The results are reported in Table V.

TABLE V

LTB$_4$ Binding Inhibition

| Example No. | $10^{-5}$ M | $10^{-6}$ M | $10^{-7}$ M |
|---|---|---|---|
| 15 | 35 | 13 | |
| 16 | 8 | −7 | |
| 18 | 5 | 3 | |
| 19 | 90 | 61 | |
| 20 | 102 | 72 | |
| 21 | 81 | 32 | |
| 23 | 85 | 50 | |
| 24 | 94 | 59 | |
| 25 | 19 | 2 | |
| 26 | 46 | 5 | |
| 28 | 77 | 32 | |
| 29 | 51 | 12 | |
| 30 | 37 | 7 | |
| 31 | 30 | 14 | |
| 36 | 40 | 7 | |
| 37 | 31 | 8 | |
| 38 | 16 | 8 | |
| 39 | 50 | 9 | |
| 40 | 31 | 8 | |
| 41 | 59 | 22 | |
| 42 | 6 | 12 | |
| 44 | 47 | 9 | |
| 45 | 51 | 15 | |
| 46 | 72 | 26 | |
| 47 | 32 | 5 | |
| 48 | 22 | 28 | |
| 49 | 47 | 15 | |
| 50 | 67 | 66 | 25 |
| 51 | 24 | 32 | |
| 53 | 5 | 13 | |
| 54 | 42 | 32 | |
| 55 | 60 | 71 | 25 |
| 56 | 42 | 15 | |
| 57 | 73 | 29 | |
| 58 | 67 | 22 | |
| 59 | 58 | 23 | |
| 60 | 12 | 6 | |
| 68 | 84 | 53 | |
| 69 | 88 | 51 | |
| 70 | 50 | 14 | |
| 71 | 30 | 17 | |
| 74 | 0 | 0 | |
| 75 | 0 | 0 | |
| 76 | 0 | 0 | |
| 77 | 71 | 23 | |
| 78 | 78 | 38 | |
| 79 | 96 | 51 | |
| 80 | 100 | 62 | |
| 81 | 71-94 | 14-59 | |
| 82 | 91 | 50 | |
| 83 | 98 | 61 | |
| 84 | 81 | 28 | |
| 85 | 86 | 37 | |
| 86 | 73 | 23 | |
| 87 | 104 | 73 | 20 |
| 88 | 19 | −1 | |
| 89 | 11 | 15 | |
| 90 | 1 | −2 | |
| 91 | 26 | 20 | |
| 92 | 40 | 20 | |
| 93 | 64 | 22 | |
| 94 | 106 | 64 | |
| 96 | 87 | 37 | |
| 97 | 91 | 53 | |
| 98 | 100 | 61 | |
| 99 | 97 | 54 | |
| 100 | 84 | 28 | |
| 101 | 101 | 82 | 45 |
| 102 | 97 | 57 | |
| 103 | 97 | 59 | |
| 104 | 32 | 5 | |
| 105 | 76 | 35 | |
| 106 | 9 | 1 | |
| 107 | 10 | 6 | |
| 108 | 105 | 96 | 60 |
| 109 | 41 | 3 | |
| 110 | 49 | 19 | |
| 114 | 52 | 8 | |
| 115 | 12-16 | 7-8 | |
| 118 | 83 | 38 | |
| 119 | 57 | 13 | |
| 120 | 97 | 55 | |
| 121 | 27-38 | 34-38 | |
| 122 | 66 | 24 | |
| 123 | 98 | 60 | |
| 125 | 10 | 6 | |
| 128 | 97 | 64 | |
| 129 | 47 | 7 | |
| 130 | 48 | 23 | |
| 132 | 0 | 0 | |
| 133 | 89 | 48 | |
| 134 | 93 | 45 | |
| 135 | 95 | 55 | |
| 136 | 100 | 77 | |
| 137 | 43 | 22 | |
| 138 | 98 | 58 | |
| 139 | 92 | 53 | |
| 140 | 94 | 59 | |
| 141 | 90 | 57 | |
| 142 | 34 | 5 | |
| 143 | 69 | 27 | |
| 144 | 63 | 20 | |
| 145 | 101 | 85 | |
| 146 | 81 | 29 | |
| 147 | 2 | 3 | |
| 148 | 44 | 14 | |
| 149 | 97 | 65 | 6 |
| 150 | 90 | 59 | |
| 151 | 105 | 103 | 78 |
| 152 | | 41 | 3 |

The compounds or formulations of the present invention may be administered by the oral and rectal routes topically parenteraerally, e.g., by injection and by continuous or discontinuous intra arterial infusion, in the form of, for example, tablets, lozenges, subingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg. (from about 5 to 50 mg. in the case of parenteral or inhalation administration, and from about 25 to 500 mg. in the case of oral or rectal administration) of a compound of Formula I. Dosages of from about 0.5 to about 300 mg./kg. per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semisolid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, :alcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, topical formulations, and those for oral ingestion.

The following formulation examples may employ as active compounds any of the compounds of this invention. The examples are illustrative only and are not intended to limit the scope of the invention in any way.

EXAMPLE 153

Hard gelatin capsules are prepared using the following ingredients:

|  | Quantity (mg/capsule) |
|---|---|
| 3-[(4-Acetyl-2-ethyl-5-hydroxyphenoxy)methyl]benzonitrile | 250 |
| Starch | 200 |
| Magnesium stearate | 10 |

The above ingredients are mixed and filled into hard gelatin capsules in 460 mg. quantities.

EXAMPLE 154

A tablet is prepared using the ingredients below:

|  | Quantity (mg/tablet) |
|---|---|
| 5-Ethyl-2-hydroxy-4-[6-methyl-6-(1H-tetrazol-5-yl)heptyloxy]acetophenone potassium salt | 250 |
| Cellulose, microcrystalline | 400 |
| Silicon dioxide, fumed | 10 |
| Magnesium stearate | 5 |

The components are blended and compressed to form tablets each weighing 665 mg.

EXAMPLE 155

An aerosol solution is prepared containing the following components:

|  | Weight % |
|---|---|
| 2-Hydroxy-4-[4-(2-methyl-2H-tetrazol-5-yl)butoxy]-5-ethylacetophenone | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred Lo a filling device. The required amount is then fed to a container and further filled with the pre-mixed propellants 12 and 114 by means of the cold-filled method or pressure-filled method. The valve units are then fitted to the container.

EXAMPLE 156

Tablets each containing 60 mg. of active ingredient are made up as follows:

| 7-(4-Acetyl-2-ethyl-5-hydroxyphenoxy)-2,2-dimethylheptanoic acid | 60 mg. |
|---|---|
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 157

Capsules each containing 80 mg. of medicament are made as follows:

| | |
|---|---|
| 2-Hydroxy-4-[6-(methylsulfonyl)-hexyloxy]-5-ethylacetophenone | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 158

Suppositories each containing 225 mg of active ingredient are made as follows:

| | |
|---|---|
| 5-[4-(4-Acetyl-2-ethyl-5-hydroxyphenoxy)butyl]-2H-tetrazole-2-acetic acid, sodium salt | 225 mg. |
| Unsaturated or saturated fatty acid glycerides to | 2,000 mg. |

The active ingredient is passed through a No. 60 mesh U.S. sieve and suspended in the fatty acid glycerides previously melted using the minimum heat necessary. The mixture is then poured into a suppository mold of nominal 2 g. capacity and allowed to cool.

EXAMPLE 159 suspensions each containing 50 mg. of medicament per 5 ml. dose are made as follows:

| | |
|---|---|
| 5-(4-Acetyl-5-hydroxy-2-allyl-phenoxy)pentanenitrile | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 ml |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

We claim:

1. A compound of the formula

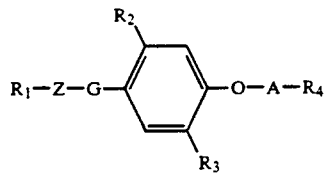

or a pharmaceutically acceptable base addition salt thereof, wherein:

$R_1$ is hydrogen or $R'OOC-$;
Z is $-(CH_2)_n-$ or phenylene;
n is 1-8;
G is $-CH_2-$, $-C(=NOH)-$ or

$R_2$ is hydroxy, halo, or $-O-(CH_2)_m-Y$;
$R_3$ is $C_1-C_6$ alkyl, $C_1-C_6$ alkanoyl, $C_2-C_4$ alkenyl, $C_1-C_4$ alkoxy, hydroxy-substituted $C_1-C_3$ alkyl, or $-CH_2-D$;
A is a bond or straight or branched chain $C_1-C_{10}$ alklidene;
$R_4$ is $C_1-C_6$ alkyl, $C_2-C_6$ alkenyl, $C_2-C_6$ alkynyl, hydroxy, [—CN,] halo, $-N_3$, $-NR_5R_6$, $-COR_7$, $-S(O)_p-(C_1-C_4$ alkyl), 1,2,4-triazol-1-yl, [5-tetrazolyl optionally substituted with a $C_2-C_4$ alkyl group or $-(CH_2)_qCOOR'$,] or phenyl optionally substituted with one or two groups selected from halo, [cyano,] $C_1-C_3$ alkyl, trifluoromethyl, [—CH_2CN,] $-CH_2Br$, $C_1-C_4$ alkoxy, $-S(O)-p-(C_1-C_4$ alkyl), acetenyl, or $-COOR'$, [5-tetrazolyl, or 5-tetrazolyl substituted with $C_1-C_4$ alkyl or $-(CH_2)_q-COOR'$];
where each $R'$ is independently hydrogen or $C_1-C_4$ alkyl;
m is 1-4;
q is 1-4;
Y is hydrogen or $-CN$;
D is halo, $C_1-C_4$ alkoxy; or $-S-(C_1-C_4$ alkyl):
$R_5$ and $R_6$ are independently hydrogen, $C_1-C_3$ alkyl, or $C_2-C_4$ alkanol, or when taken together with the nitrogen atom to which they are attached form a morpholino ring;
$R_7$ is hydroxy, $C_1-C_4$ alkoxy, halo, $-NR_5R_6$, $-NHOH$, $-N(CH_3)OH$,

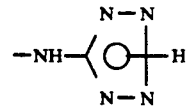

each p is 0, 1, or 2,
provided that when A is a bond, $R_4$ must be $C_1-C_6$ alkyl or an optionally substituted phenyl group, and further provided that when one of $R_5$ and $R_6$ is $C_2-C_4$ alkanoyl, the other of $R_5$ and $R_6$ is hydrogen.

2. A compound of claim 1 of the formula

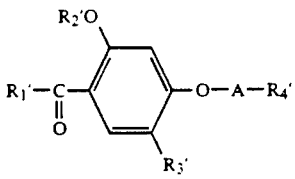

and pharmaceutically acceptable base addition salts thereof
wherein
$R_1'$ is methyl or ethyl;
$R_2'$ is hydrogen or methyl;
$R_3'$ is ethyl, propyl, —$CH_2$—S—$CH_3$, or allyl; and
$R_4'$ is hydroxy, —COOR', —$CONR_5R_6$; —CO($C_1$-$C_3$ alkyl), —$S(O)_p$—($C_1$-$C_4$ alkyl), or phenyl optionally substituted in the meta position with halo, $C_1$-$C_3$ alkyl, trifluoromethyl, —$CH_2Br$, $C_1C_4$ alkoxy, —$S(O)_p$-($C_1$-$C_4$ alkyl), acetyl, or —COOR'.

3. The compound of claim 2 which is 7-(4-acetyl-2-ethyl-5-hydroxyphenoxy)-2,2-dimethylheptanoic acid or a pharmaceutically acceptable base addition salt thereof.

4. The compound of claim 2 which is 2-hydroxy-4-5-ethylacetophenone.

5. A method of treating inflammation in a mammal which comprises administering to said mammal an effective amount of a compound of claim 1.

6. A method of treating inflammation in a mammal which comprises administering to said mammal an effective amount of a compound of claim 2.

7. The method of claim 6 employing 7-(4-acetyl-2-ethyl-5-hydroxyphenoxy)-2,2-dimethylheptanoic acid or a pharmaceutically acceptable base addition salt thereof.

8. The method of claim 6 employing 2-hydroxy-4-5-ethylacetophenone.

9. A pharmaceutical formulation comprising an effective amount of a compound of claim 1 in association with a pharmaceutically acceptable carrier.

10. A pharmaceutical formulation comprising an effective amount of a compound of claim 2 in association with a pharmaceutically acceptable carrier.

11. A formulation according to claim 10 employing 7-(4-acetyl-2-ethyl-5-hydroxyphenoxy)-2,2-dimethylheptanoic acid or a pharmaceutically acceptable base addition salt thereof.

12. A formulation according to claim 10 employing 2-hydroxy-4-5-ethylacetophenone.

13. A method of treating psoriasis in a mammal which comprises administering to said mammal an effective amount of a compound of claim 1.

14. A method of antagonizing $LTB_4$ receptors in a mammal which comprises administering to said mammal an effective amount of a compound of claim 1.

* * * * *

UNITED STATES PATENT AND TRADEMARK OFFICE
CERTIFICATE OF CORRECTION

PATENT NO. : 5,098,613
DATED : March 24, 1992
INVENTOR(S) : Nancy G. Bollinger, et al.

It is certified that error appears in the above-identified patent and that said Letters Patent is hereby corrected as shown below:

Claim 1, column 38, line 28, please change "alklidene" to read --alkylidene--.

Claim 1, Column 38, line 31, please delete "[-CN,]".

Claim 1, column 38, lines 31-33, please delete "[5-tetrazolyl optionally substituted with a $C_2$-$C_4$ alkyl group or -$(CH_2)_q$ COOR',]".

Claim 1, column 38, line 36, please delete "[cyano,]".

Claim 1, column 38, line 37, please delete "[-$CH_2CN$,]".

Claim 1, column 38, lines 30-40, please delete "[5-tetrazolyl, or 5-tetrazolyl substituted with $C_1$-$C_4$ alkyl or -$(CH_2)_q$-COOR']".

Claim 1, column 38, line 59, following the structure please insert ", or $C_1$-$C_3$ alkyl; and".

Signed and Sealed this

Eighth Day of June, 1993

Attest:

MICHAEL K. KIRK

*Attesting Officer*   *Acting Commissioner of Patents and Trademarks*